US012611468B2

(12) United States Patent
Hobbs et al.

(10) Patent No.: US 12,611,468 B2
(45) Date of Patent: *Apr. 28, 2026

(54) RECOMBINANT ADENO-ASSOCIATED VIRUS VECTORS TO TARGET MEDULLARY THYROID CARCINOMA

(71) Applicant: University of Florida Research Foundation, Incorporated, Gainesville, FL (US)

(72) Inventors: Jacqueline A. Hobbs, Gainesville, FL (US); Scott A. Rivkees, Gainesville, FL (US); Arun Srivastava, Gainesville, FL (US); Laura Adamson, Cambridge, MA (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 1113 days.

This patent is subject to a terminal disclaimer.

(21) Appl. No.: 17/590,557

(22) Filed: Feb. 1, 2022

(65) Prior Publication Data

US 2022/0233719 A1 Jul. 28, 2022

Related U.S. Application Data

(63) Continuation of application No. 15/741,253, filed as application No. PCT/US2016/040687 on Jul. 1, 2016, now Pat. No. 11,266,748.

(60) Provisional application No. 62/188,191, filed on Jul. 2, 2015.

(51) Int. Cl.
| | |
|---|---|
| *A61K 48/00* | (2006.01) |
| *A61P 35/00* | (2006.01) |
| *C12N 15/86* | (2006.01) |

(52) U.S. Cl.
CPC .......... *A61K 48/0058* (2013.01); *A61P 35/00* (2018.01); *C12N 15/86* (2013.01); *C12N 2750/14122* (2013.01); *C12N 2750/14143* (2013.01); *C12N 2830/008* (2013.01)

(58) Field of Classification Search
CPC ............................... A61K 48/00; C12N 15/86
See application file for complete search history.

(56) References Cited

U.S. PATENT DOCUMENTS

| | | | | |
|---|---|---|---|---|
| 11,266,748 B2 * | 3/2022 | Hobbs et al. | ...... | A61K 48/0058 |
| 2003/0223971 A1 * | 12/2003 | Kurtzman et al. | ..... | A61K 48/00 424/93.21 |
| 2011/0065100 A1 | 3/2011 | Aldred et al. | | |

| | | | | |
|---|---|---|---|---|
| 2013/0310443 A1 * | 11/2013 | Srivastava et al. | .. | C07K 14/005 514/44 R |
| 2014/0127180 A1 * | 5/2014 | De Waziers et al. | ...................... | C12N 9/0071 424/94.2 |
| 2014/0341852 A1 | 11/2014 | Srivastava et al. | | |

OTHER PUBLICATIONS

Wu et al. (1994) "Treatment of advanced medullary thyroid carcinoma with a combination of cyclophosphamide, vincristine, and dacarbazine" Cancer, 73(2), 432-436. (Year: 1994).*

Zhu et al. (2024) "Quantitative analysis of transcription start site selection reveals control by DNA sequence, RNA polymerase II activity and NTP levels" Nature Structural & Molecular Biology, 31(1), 190-202. (Year: 2024).*

Freaney et al. (2014) "High-density nucleosome occupancy map of human chromosome 9p21-22 reveals chromatin organization of the type I interferon gene cluster" Journal of Interferon & Cytokine Research, 34(9), 676-685. (Year: 2014).*

Jiang et al. (2001) "Tissue-specific gene expression in medullary thyroid carcinoma cells employing calcitonin regulatory elements and AAV vectors" Cancer gene therapy, 8(7), 469-472. (Year: 2001).*

Grimm et al. (1998) "Novel tools for production and purification of recombinant adenoassociated virus vectors" Human gene therapy , 9(18), 2745-2760. (Year: 1998).*

Messina et al. (2000) "High level, tissue-specific expression of a modified calcitonin/calcitonin gene-related peptide promoter in a human medullary thyroid carcinoma cell line" Molecular and cellular endocrinology, 164:219-224. (Year: 2000).*

International Search Report and Written Opinion for Application No. PCT/US2016/040687 mailed on Oct. 4, 2016.

International Preliminary Report on Patentability for Application No. PCT/US2016/040687 mailed on Jan. 11, 2018.

Jiang et al., Tissue-specific gene expression in medullary thyroid carcinoma cells employing calcitonin regulatory elements and AAV vectors. Cancer Gene Therapy. Jul. 1, 2001;8:469-72.

Liu et al., Characterization of CYP2B6 in a CYP2B6-humanized mouse model: inducibility in the liver by phenobarbital and dexamethasone and role in nicotine metabolism in vivo. Drug Metabolism and Disposition. Feb. 2015;43:208-216.

* cited by examiner

*Primary Examiner* — James Joseph Graber
(74) *Attorney, Agent, or Firm* — Wolf, Greenfield & Sacks, P.C.

(57) ABSTRACT

Provided herein are nucleic acids, recombinant adeno-associated virus (rAAV) particles, and compositions, as well as methods of use thereof for transducing medullary thyroid carcinoma cells and in treatment of disease, such as medullary thyroid carcinoma. In some aspects, the nucleic acid comprises a truncated calcitonin promoter, which is optionally encapsidated within a rAAV particle. In other aspects, the rAAV particle is a rAAV particle having a mutation in a surface-exposed amino acid, such as tyrosine, threonine, or serine, that enhances transduction of the particle into medullary thyroid carcinoma cells.

10 Claims, 7 Drawing Sheets

Specification includes a Sequence Listing.

FIG. 4A                FIG. 4B
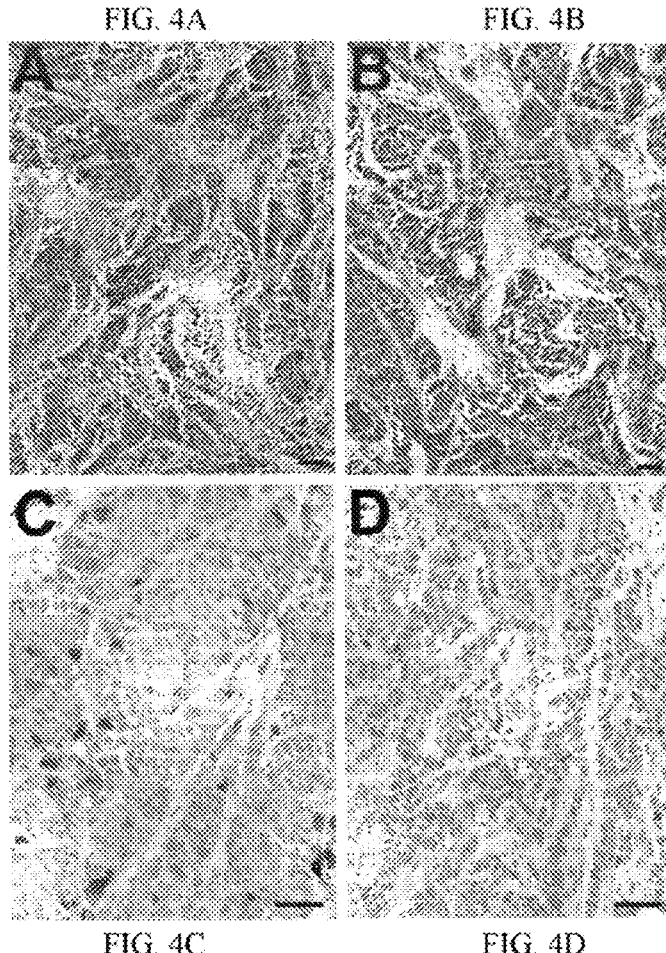
FIG. 4C                FIG. 4D
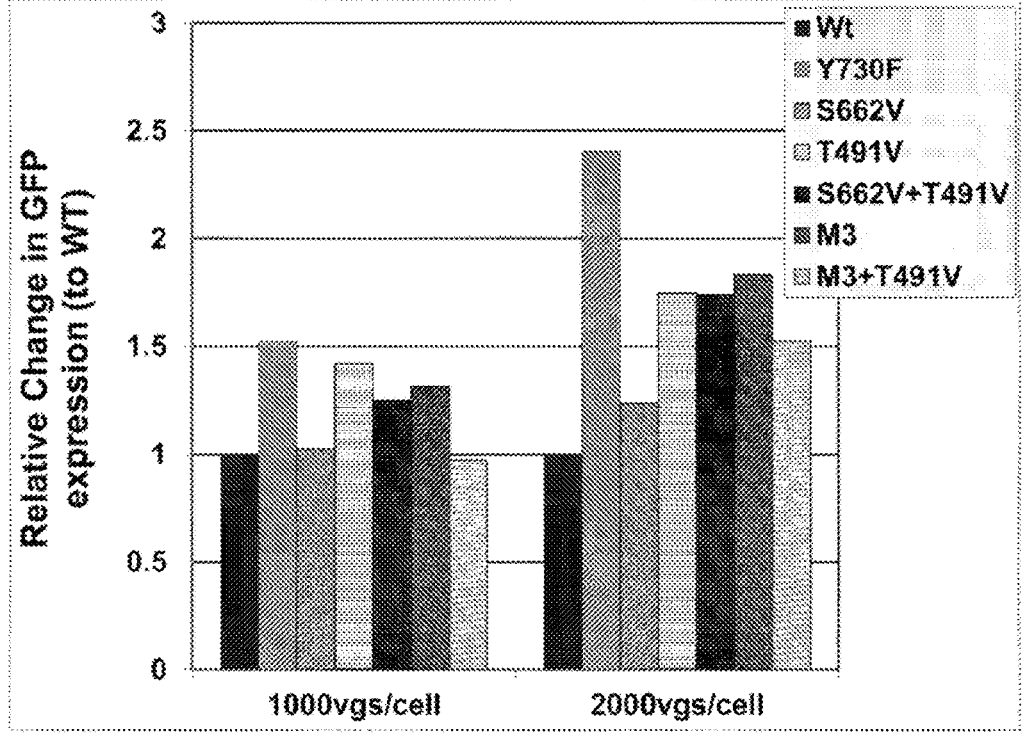
FIG. 5

SEQUENCE LISTING

```
<160> NUMBER OF SEQ ID NOS: 15

<210> SEQ ID NO 1
<211> LENGTH: 290
<212> TYPE: DNA
<213> ORGANISM: Homo sapiens

<400> SEQUENCE: 1
ttccatcaat gacctcaatg caaatacaag tgggacggtc ctgctggatc ctccaggttc        60
tggaagcatg agggtgacgc aacccagggg caaaggaccc ctccgcccat tggttgctgt       120
gcactggcgg aactttcccg acccacagcg gcgggaataa gagcagtcgc tggcgctggg       180
aggcatcaga gacactgccc agcccaagtg tcgccgccgc ttccacaggg ctctggctgg       240
acgccgccgc cgccgctgcc accgcctctg atccaagcca cctcccgcca                   290
```

-continued

```
<210> SEQ ID NO 2
<211> LENGTH: 735
<212> TYPE: PRT
<213> ORGANISM: Adeno-associated virus 2

<400> SEQUENCE: 2

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
        130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
```

```
              370              375              380
Gln Ala Val Gly Arg Ser Ser Phe Tyr Cys Leu Glu Tyr Phe Pro Ser
385              390              395              400

Gln Met Leu Arg Thr Gly Asn Asn Phe Thr Phe Ser Tyr Thr Phe Glu
                 405              410              415

Asp Val Pro Phe His Ser Ser Tyr Ala His Ser Gln Ser Leu Asp Arg
                 420              425              430

Leu Met Asn Pro Leu Ile Asp Gln Tyr Leu Tyr Tyr Leu Ser Arg Thr
                 435              440              445

Asn Thr Pro Ser Gly Thr Thr Thr Gln Ser Arg Leu Gln Phe Ser Gln
                 450              455              460

Ala Gly Ala Ser Asp Ile Arg Asp Gln Ser Arg Asn Trp Leu Pro Gly
465              470              475              480

Pro Cys Tyr Arg Gln Gln Arg Val Ser Lys Thr Ser Ala Asp Asn Asn
                 485              490              495

Asn Ser Glu Tyr Ser Trp Thr Gly Ala Thr Lys Tyr His Leu Asn Gly
                 500              505              510

Arg Asp Ser Leu Val Asn Pro Gly Pro Ala Met Ala Ser His Lys Asp
                 515              520              525

Asp Glu Glu Lys Phe Phe Pro Gln Ser Gly Val Leu Ile Phe Gly Lys
                 530              535              540

Gln Gly Ser Glu Lys Thr Asn Val Asp Ile Glu Lys Val Met Ile Thr
545              550              555              560

Asp Glu Glu Glu Ile Arg Thr Thr Asn Pro Val Ala Thr Glu Gln Tyr
                 565              570              575

Gly Ser Val Ser Thr Asn Leu Gln Arg Gly Asn Arg Gln Ala Ala Thr
                 580              585              590

Ala Asp Val Asn Thr Gln Gly Val Leu Pro Gly Met Val Trp Gln Asp
                 595              600              605

Arg Asp Val Tyr Leu Gln Gly Pro Ile Trp Ala Lys Ile Pro His Thr
                 610              615              620

Asp Gly His Phe His Pro Ser Pro Leu Met Gly Gly Phe Gly Leu Lys
625              630              635              640

His Pro Pro Pro Gln Ile Leu Ile Lys Asn Thr Pro Val Pro Ala Asn
                 645              650              655

Pro Ser Thr Thr Phe Ser Ala Ala Lys Phe Ala Ser Phe Ile Thr Gln
                 660              665              670

Tyr Ser Thr Gly Gln Val Ser Val Glu Ile Glu Trp Glu Leu Gln Lys
                 675              680              685

Glu Asn Ser Lys Arg Trp Asn Pro Glu Ile Gln Tyr Thr Ser Asn Tyr
                 690              695              700

Asn Lys Ser Val Asn Val Asp Phe Thr Val Asp Thr Asn Gly Val Tyr
705              710              715              720

Ser Glu Pro Arg Pro Ile Gly Thr Arg Tyr Leu Thr Arg Asn Leu
                 725              730              735
```

<210> SEQ ID NO 3
<211> LENGTH: 2208
<212> TYPE: DNA
<213> ORGANISM: Homo sapiens

<400> SEQUENCE: 3

```
gatccggggc tcattgtgcc caagatccgc catccaagcc ctgctctgcg cgcagcttgc    60
ctgtttcacg ctctgcgcct gacacgcgcc ggtgtcctcc cgggccagtt ccagtcccgg   120
```

```
gtcctgtggc cgccctgccg gcggaccctg cggagagcga gtcttagata cccagtcccc          180
agccccgagt tgttattccc tcgctgtagt taagaaggag gagatcaatt aagggcatct          240
tagaagttag gcgttcccgc tgcctccttt gagcacggag gccaccaacc ccctaggggg          300
aagagatgta gcgcgaggca ggggtgtcgt gctaagaaat ttcgacgctt ctggggactg          360
aggacaaagg tgcggacacg accccggggt acctggagtt ccgtgactcg cgccacggac          420
ggcacaccta ggggctaatt tctgctctgc ctcaaagaac ctcaagctag agtccttgcc          480
tccgcccaca gccccgggat gccgctgctg cgctcaccgc acaggcagcg cccggaccgg          540
ctgcagcaga tcgcgcgctg cgcgttccac cgggagatgg tggagacgct gaaaagcttc          600
tttcttgcca ctctggacgc tgtgggcggc aagcgcctta gtccctacct ctgctgagct          660
gaacgctcag gcacagtgga actgaaaccc ggttctgcgg gatgtgagag ctgttgaggt          720
cacgcgtaat tgggtgtgat ggagggcgcc tgttcgtgat gtgtgcaggt ttgatgcaag          780
caggtcatcg tcgtgcgagt gtgtggatgc gaccgcccga gagactcgga ggcaggcttg          840
ggacacgttt gagtgaacac ctcaggatac tcttctggcc agtatctgtt ttttagtgtc          900
tgtgattcag agtgggcaca tgttgggaga cagtaatggg tttgggtgtg tgtaaatgag          960
tgtgaccgga agcgagtgtg agcttgatct aggcagggac cacacagcac tgtcacacct         1020
gcctgctctt tagtagagga ctgaagtgcg ggggtggggg tacggggccg gaatagaatg         1080
tctctgggac atcttggcaa acagcagccg gaagcaaagg ggcagctgtg caaacggctc         1140
aggcaggtga tggatggcag ggtaggaagg gggaggtcca gaggtctgga tggaggcttc         1200
cgcatctgta ccttgcaact cacccctcag gcccagcagg tcatcggccc cctcctcaca         1260
catgtaatgg atctgaagag taccccggga cagtccgggg agatggagat tcggaaagta         1320
tccatggaga tcttacagaa tcccctgtgc ggaccaggaa actcttgtag atccctgcct         1380
atctgaggcc caggcgctgg gctgtttctc acaatattcc ttcaagatga gattgtggtc         1440
cccatttcaa agatgagtac actgagcctc tgtgaagtta cttgcccatg atcacacaac         1500
caggaattgg gccaactgta attgaactcc tgtctaacaa agttcttgct cccagctccg         1560
tctcttgttt cccacgagcc ctggccctct gtgggtaata ccagctactg gagtcagatt         1620
tcttgggccc agaacccacc cttaggggca ttaaccttta aaatctcact tgggcagggg         1680
tctgggatca gagttggaag agtccctaca atcctggacc ctttccgcca aatcgtgaaa         1740
ccaggggtgg agtggggcga gggttcaaaa ccaggccgga ctgagaggtg aaattcacca         1800
tgacgtcaaa ctgccctcaa attcccgctc actttaaggg cgttacttgt tggtgccccc         1860
accatccccc accatttcca tcaatgacct caatgcaaat acaagtggga cggtcctgct         1920
ggatcctcca ggtctggaa gcatgagggt gacgcaaccc aggggcaaag gacccctccg         1980
cccattggtt gctgtgcact ggcggaactt tcccgaccca cagcggcggg aataagagca         2040
gtcgctggcg ctgggaggca tcagagacac tgcccagccc aagtgtcgcc gccgcttcca         2100
cagggctctg gctggacgcc gccgccgccg ctgccaccgc ctctgatcca agccacctcc         2160
cgccaggtga gccccgagat cctggctcag gtatatgtct ctccctcc                     2208
```

<210> SEQ ID NO 4
<211> LENGTH: 3053
<212> TYPE: DNA
<213> ORGANISM: Homo sapiens
<400> SEQUENCE: 4

```
caggaccatg gaactcagcg tcctcctctt ccttgcactc ctcacaggac tcttgctact      60
cctggttcag cgccacccta acacccatga ccgcctccca ccagggcccc gccctctgcc     120
ccttttggga aaccttctgc agatggatag aagaggccta ctcaaatcct ttctgaggtt     180
ccgagagaaa tatggggacg tcttcacggt acacctggga ccgaggcccg tggtcatgct     240
gtgtggagta gaggccatac gggaggccct tgtggacaag gctgaggcct tctctggccg     300
gggaaaaatc gccatggtcg acccattctt ccggggatat ggtgtgatct ttgccaatgg     360
aaaccgctgg aaggtgcttc ggcgattctc tgtgaccact atgagggact cgggatggg     420 aaagcggagt gtggaggagc ggattcagga ggaggctcag tgtctgatag aggagcttcg     480
gaaatccaag ggggccctca tggaccccac cttcctcttc cagtccatta ccgccaacat     540
catctgctcc atcgtctttg aaaacgatt ccactaccaa gatcaagagt tcctgaagat     600
gctgaacttg ttctaccaga cttttttcact catcagctct gtattcggcc agctgtttga     660
gctcttctct ggcttcttga aatactttcc tggggcacac aggcaagttt acaaaaaacct     720 gcaggaaatc aatgcttaca ttggccacag tgtggagaag caccgtgaaa ccctggaccc     780
cagcgccccc aaggacctca tcgacaccta cctgctccac atggaaaaag agaaatccaa     840
cgcacacagt gaattcagcc accagaacct caacctcaac acgctctcgc tcttctttgc     900
tggcactgag accaccagca ccactctccg ctacggcttc ctgctcatgc tcaaataccc     960
tcatgttgca gagagagtct acaggggagat tgaacaggtg attggcccac atcgccctcc    1020
agagcttcat gaccgagcca aaatgccata cacagaggca gtcatctatg agattcagag    1080
attttccgac cttctcccca tgggtgtgcc ccacattgtc acccaacaca ccagcttccg    1140
agggtacatc atccccaagg acacagaagt atttctcatc ctgagcactg ctctccatga    1200
cccacactac tttgaaaaac cagacgcctt caatcctgac cacttctgg atgccaatgg    1260 ggcactgaaa aagactgaag cttttatccc cttctcctta gggaagcgga tttgtcttgg    1320
tgaaggcatc gcccgtgcgg aattgttcct cttcttcacc accatcctcc agaacttctc    1380
catggccagc cccgtggccc cagaagacat cgatctgaca ccccaggagt gtggtgtggg    1440 caaaatacccc ccaacatacc agatccgctt cctgccccgc tgaaggggct gagggaaggg    1500
ggtcaaagga ttccagggtc attcagtgtc cccgcctctg tagacaatgg ctctgactcc    1560
cccgcaactt cctgcctctg agagacctgc tacaagccag cttccttccc tccatggca    1620 ccagttgtct gaggtcacat tgcaagtgag tgcaggagtg agattatcga aaattataat    1680
atacaaaatc atatatatat atatgttctt gtttttttgag acagagtctc acactgttgc    1740
ccaggctgga gtgcagtggc gtgatctcgg ctcactgcaa cctccacccc cggggatcaa    1800
gcaactctcc tgcctcagcc tccctagtag ctgggattac aggcatgcac taccacgctt    1860
ggctaatttt tgtattttta gtagagatgg ggtttcactg tgtaggccag gctggtctcg    1920
aactcctgaa ctcaagtgat tcacccacct tagcctccca aagtgctggg attacaggcg    1980
tgagtcaccg tgcccagcca tgtatatata aattttaaa aattaagctg aaattcacat    2040
aacataaaat tagctgtttt aaagtgtaaa atttagtggc gtgtggttca ttcacaaagc    2100
tgtacaacca ccaccatcta gttccaaaca ttttcttttt ttctgagatg gagtctcact    2160
ctgtcaccca ggttcgagtt cagtggtgcc atctctgtcc actgcaacct ccacatcctg    2220
ggttcaagtg attctcctgc ctcagcctct ggaggagctg gtatcacagg cgtcccccac    2280
cacgcctggc taaattttgt attttttaggt ggtcttgaac tcctgatgtc aggtgattct    2340
cctagctcca aatgttttca ttatctctcc cccaacaaaa cccataccta tcaagctgtc    2400
```

-continued

```
actccccata ccccattctc tttttcatct cggcccctgt caatctggtt tttgtcacta     2460
tggacttacc aattctgaat atttcccata aacagaatca tacaatattt gatttttttt     2520
ttttttttga aactaagcct tgctctgtct cccaggctgg agtgctatgg tgcaattttt     2580
gttcactgca acctctgcct tccaagatca agagattctc cagtctcagc tcccaagtag     2640
ctgggattac aggcatgtac taccatgcct ggctaatttt cttgtagttt tagtagggac     2700
atgttggcca ggctggtggt gagctcctgg cctcaggtga tccacccacc tcagtgttcc     2760
aaagtgctga tattacaggc ataatatgtg atcttttgtg tctggttgct ttcatgttga     2820
atgctatttt tgaggttcat gcctgttgta gaccacagtc acacactgct gtagtcttcc     2880
ccagtcctca ttcccagctg cctcttccta ctgcttccgt ctatcaaaaa gccccttgg      2940 cccaggttcc ctgagctgtg ggattctgca ctggtgcttt ggattccctg atatgttcct     3000
tcaaatctgc tgagaattaa ataaacatct ctaaagcctg acctccccac gtc            3053
```

<210> SEQ ID NO 5
<211> LENGTH: 145
<212> TYPE: DNA
<213> ORGANISM: Adeno-associated virus 2

<400> SEQUENCE: 5

```
ttggccactc cctctctgcg cgctcgctcg ctcactgagg ccgggcgacc aaaggtcgcc       60
cgacgcccgg gctttgcccg ggcggcctca gtgagcgagc gagcgcgcag agagggagtg      120
gccaactcca tcactagggg ttcct                                            145
```

<210> SEQ ID NO 6
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 6

```
caggggtgtc gtgctaagaa                                                   20
```

<210> SEQ ID NO 7
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 7

```
ccagaatctc ggggctcacc t                                                 21
```

<210> SEQ ID NO 8
<211> LENGTH: 531
<212> TYPE: DNA
<213> ORGANISM: Artificial Sequence
<220> FEATURE:
<223> OTHER INFORMATION: Synthetic Polynucleotide

<400> SEQUENCE: 8

```
gatctgagct tgatctaggc agggaccaca cagcactgtc acacctgcct gctctttagt       60
agaggactga agtgcggggg tgggggtacg gggccggaat agaatgtctc tgggacatct      120
tggcaaacag cagccggaag caaaggggca gctgtgcaaa cggctcaggc aggtgatgga      180
tggcagggta ggaaggggga gccagaggtc tggatggagg ttctagattt tccatcaatg      240
```

-continued

```
acctcaatgc aaatacaagt gggacggtcc tgctggatcc tccaggttct ggaagcatga        300
gggtgacgca acccaggggc aaaggacccc tccgcccatt ggttgctgtg cactggcgga        360
actttcccga cccacagcgg cgggaataag agcagtcgct ggcgctggga ggcatcagag        420
acactgccca gcccaagtgt cgccgccgct tccacagggc tctggctgga cgccgccgcc        480
gccgctgcca ccgcctctga tccaagccac ctcccgccac tagtgatatc a        531
```

```
<210> SEQ ID NO 9
<211> LENGTH: 759
<212> TYPE: DNA
<213> ORGANISM: Artificial Sequence
<220> FEATURE:
<223> OTHER INFORMATION: Synthetic Polynucleotide

<400> SEQUENCE: 9
gatctgagct tgatctaggc agggaccaca cagcactgtc acacctgcct gctctttagt         60
agaggactga agtgcggggg tggggtacg gggccggaat agaatgtctc tgggacatct        120
tggcaaacag cagccggaag caaaggggca gctgtgcaaa cggctcaggc aggtgatgga        180
tggcagggta ggaaggggga gccagaggtc tggatggagg ttctagcaga tctgagcttg        240
atctaggcag ggaccacaca gcactgtcac acctgcctgc tctttagtag aggactgaag        300
tgcgggggtg ggggtacggg gccggaatag aatgtctctg gacatcttg gcaaacagca        360 gccggaagca aaggggcagc tgtgcaaacg gctcaggcag gtgatggatg cagggtagg        420 aaggggagc cagaggtctg gatggaggtt ctagattttc catcaatgac ctcaatgcaa        480
atacaagtgg gacggtcctg ctggatcctc caggttctgg aagcatgagg gtgacgcaac        540 ccagggggcaa aggacccctc cgcccattgg ttgctgtgca ctggcggaac tttcccgacc        600
cacagcggcg ggaataagag cagtcgctgg cgctgggagg catcagagac actgcccagc        660
ccaagtgtcg ccgccgcttc cacagggctc tggctggacg ccgccgccgc cgctgccacc        720
gcctctgatc caagccacct cccgccacta gtgatatca        759
```

```
<210> SEQ ID NO 10
<211> LENGTH: 480
<212> TYPE: DNA
<213> ORGANISM: Artificial Sequence
<220> FEATURE:
<223> OTHER INFORMATION: Synthetic Polynucleotide

<400> SEQUENCE: 10
gatctgagct tgatctaggc agggaccaca cagcactgtc acacctgcct gctctttagt         60
agaggactga agtgcggggg tggggtacg gggccggaat agaatgtctc tgggacatct        120
tggcaaacag cagccggaag caaaggggca gctgtgcaaa cggctcaggc aggtgatgga        180
tggcagggta ggaaggggga gccagaggtc tggatggagg tttggatcct ccaggttctg        240
gaagcatgag ggtgacgcaa cccagggggca aggacccct ccgcccattg gttgctgtgc        300
actggcggaa ctttcccgac ccacagcggc gggaataaga gcagtcgctg cgctgggag        360 gcatcagaga cactgcccag cccaagtgtc gccgccgctt ccacagggct ctggctggac        420
gccgccgccg ccgctgccac cgcctctgat ccaagccacc tcccgccact agtgatatca        480
```

```
<210> SEQ ID NO 11
<211> LENGTH: 708
<212> TYPE: DNA
<213> ORGANISM: Artificial Sequence
<220> FEATURE:
<223> OTHER INFORMATION: Synthetic Polynucleotide
```

<400> SEQUENCE: 11
gatctgagct tgatctaggc agggaccaca cagcactgtc acacctgcct gctctttagt     60
agaggactga agtgcggggg tgggggtacg gggccggaat agaatgtctc tgggacatct    120
tggcaaacag cagccggaag caaaggggca gctgtgcaaa cggctcaggc aggtgatgga    180
tggcagggta ggaagggga gccagaggtc tggatggagg ttctagcaga tctgagcttg    240
atctaggcag ggaccacaca gcactgtcac acctgcctgc tctttagtag aggactgaag    300
tgcgggggtg ggggtacggg gccggaatag aatgtctctg gacatcttg gcaaacagca    360 gccggaagca aaggggcagc tgtgcaaacg gctcaggcag gtgatggatg gcaggggtagg    420 aaggggagc cagaggtctg gatggaggtt ggatcctcc aggttctgga agcatgaggg    480
tgacgcaacc caggggcaaa ggacccctcc gcccattggt tgctgtgcac tggcggaact    540
ttcccgaccc acagcggcgg gaataagagc agtcgctggc gctgggaggc atcagagaca    600
ctgcccagcc caagtgtcgc cgccgcttcc acagggctct ggctggacgc cgccgccgcc    660
gctgccaccg cctctgatcc aagccacctc ccgccactag tgatatca             708

<210> SEQ ID NO 12
<211> LENGTH: 308
<212> TYPE: DNA
<213> ORGANISM: Homo sapiens

<400> SEQUENCE: 12
ttccatcaat gacctcaatg caaatacaag tgggacggtc ctgctggatc ctccaggttc     60
tggaagcatg agggtgacgc aacccagggg caaaggaccc ctccgcccat tggttgctgt    120
gcactggcgg aactttcccg acccacagcg gcgggaataa gagcagtcgc tggcgctggg    180
aggcatcaga gacactgccc agcccaagtg tcgccgccgc ttccacaggg ctctggctgg    240
acgccgccgc cgccgctgcc accgcctctg atccaagcca cctcccgcca ggtgagcccc    300
gagatcct                                                             308

<210> SEQ ID NO 13
<211> LENGTH: 264
<212> TYPE: DNA
<213> ORGANISM: Homo sapiens

<400> SEQUENCE: 13
tggatcctcc aggttctgga agcatgaggg tgacgcaacc caggggcaaa ggacccctcc     60
gcccattggt tgctgtgcac tggcggaact ttcccgaccc acagcggcgg gaataagagc    120
agtcgctggc gctgggaggc atcagagaca ctgcccagcc caagtgtcgc cgccgcttcc    180
acagggctct ggctggacgc cgccgccgcc gctgccaccg cctctgatcc aagccacctc    240
ccgccaggtg agccccgaga tcct                                            264

<210> SEQ ID NO 14
<211> LENGTH: 221
<212> TYPE: DNA
<213> ORGANISM: Homo sapiens

<400> SEQUENCE: 14
gagcttgatc taggcaggga ccacacagca ctgtcacacc tgcctgctct ttagtagagg     60
actgaagtgc gggggtgggg gtacgggccc ggaatagaat gtctctggga catcttggca    120
aacagcagcc ggaagcaaag gggcagctgt gcaaacggct caggcaggtg atggatggca    180

-continued

```
gggtaggaag ggggaggtcc agaggtctgg atggaggctt c                     221

<210> SEQ ID NO 15
<211> LENGTH: 1863
<212> TYPE: DNA
<213> ORGANISM: Homo sapiens

<400> SEQUENCE: 15
gggtgtcgtg ctaagaaatt tcgacgcttc tggggactga ggacaaaggt gcggacacga     60
ccccggggta cctggagttc cgtgactcgc gccacggacg gcacacctag gggctaattt    120
ctgctctgcc tcaaagaacc tcaagctaga gtccttgcct ccgcccacag ccccgggatg    180
ccgctgctgc gctcaccgca caggcagcgc ccggaccggc tgcagcagat cgcgcgctgc    240
gcgttccacc gggagatggt ggagacgctg aaaagcttct ttcttgccac tctggacgct    300
gtgggcggca agcgccttag tccctacctc tgctgagctg aacgctcagg cacagtggaa    360
ctgaaacccg gttctgcggg atgtgagagc tgttgaggtc acgcgtaatt gggtgtgatg    420
gagggcgcct gttcgtgatg tgtgcaggtt tgatgcaagc aggtcatcgt cgtgcgagtg    480
tgtggatgcg accgcccgag agactcggag gcaggcttgg gacacgtttg agtgaacacc    540
tcaggatact cttctggcca gtatctgttt tttagtgtct gtgattcaga gtgggcacat    600
gttgggagac agtaatgggt ttgggtgtgt gtaaatgagt gtgaccggaa gcgagtgtga    660
gcttgatcta ggcagggacc acacagcact gtcacacctg cctgctcttt agtagaggac    720
tgaagtgcgg gggtgggggt acggggccgg aatagaatgt ctctgggaca tcttggcaaa    780
cagcagccgg aagcaaaggg gcagctgtgc aaacggctca ggcaggtgat ggatggcagg    840
gtaggaaggg ggaggtccag aggtctggat ggaggcttcc gcatctgtac cttgcaactc    900
acccctcagg cccagcaggt catcggcccc ctcctcacac atgtaatgga tctgaagagt    960
accccgggac agtccgggga gatggagatt cggaaagtat ccatggagat cttacagaat   1020
cccctgtgcg gaccaggaaa ctcttgtaga tccctgccta tctgaggccc aggcgctggg   1080
ctgtttctca caatattcct tcaagatgag attgtggtcc ccatttcaaa gatgagtaca   1140
ctgagcctct gtgaagttac ttgcccatga tcacacaacc aggaattggg ccaactgtaa   1200
ttgaactcct gtctaacaaa gttcttgctc ccagctccgt ctcttgtttc ccacgagccc   1260
tggccctctg tgggtaatac cagctactgg agtcagattt cttgggccca gaacccaccc   1320 ttagggggcat taacctttaa aatctcactt gggcagggggt ctgggatcag agttggaaga   1380
gtccctacaa tcctggaccc tttccgccaa atcgtgaaac caggggtgga gtggggcgag   1440
ggttcaaaac caggccggac tgagaggtga aattcaccat gacgtcaaac tgccctcaaa   1500
ttcccgctca ctttaagggc gttacttgtt ggtgccccca ccatcccca ccatttccat    1560 caatgacctc aatgcaaata caagtgggac ggtcctgctg gatcctccag gttctggaag   1620
catgagggtg acgcaaccca ggggcaaagg accctccgc ccattggttg ctgtgcactg    1680
gcggaacttt cccgacccac agcggcggga ataagagcag tcgctggcgc tgggaggcat   1740
cagagacact gcccagccca agtgtcgccg ccgcttccac agggctctgg ctggacgccg   1800
ccgccgccgc tgccaccgcc tctgatccaa gccacctccc gccaggtgag ccccgagatc   1860
ctg                                                               1863
```

RECOMBINANT ADENO-ASSOCIATED VIRUS VECTORS TO TARGET MEDULLARY THYROID CARCINOMA

RELATED APPLICATIONS

This application is a continuation application of U.S. application Ser. No. 15/741,253, filed Dec. 30, 2017, entitled "RECOMBINANT ADENO-ASSOCIATED VIRUS VECTORS TO TARGET MEDULLARY THYROID CARCINOMA", which is a National Stage Application of PCT/US2016/040687, filed Jul. 1, 2016, which claims the benefit under 35 U.S.C. § 119(e) of U.S. provisional application Ser. No. 62/188,191, filed Jul. 2, 2015, entitled "RECOMBINANT ADENO-ASSOCIATED VIRUS VECTORS TO TARGET MEDULLARY THYROID CARCINOMA", the entire contents of each of which is incorporated by reference herein.

BACKGROUND OF THE INVENTION

Medullary thyroid carcinomas (MTC) originate in parafollicular, or C cells, of the thyroid. MTC often presents with metastatic disease and once metastasized, are incurable.

SUMMARY OF THE INVENTION

Aspects of the disclosure relate to nucleic acids, recombinant adeno-associated virus (rAAV) particles, compositions, and methods related to gene therapy for medullary thyroid carcinoma (MTC).

As described herein, it was found that a truncated calcitonin promoter was capable of driving higher expression levels in MTC cells than the full wild-type calcitonin promoter and was specific for MTC cells. Further it was determined that capsid-modified rAAV2 viral particles containing one or more mutations in surface-exposed tyrosine, serine, or threonine residues transduced MTC cells with higher efficiency than wild-type rAAV2 viral particles. Lastly, it was shown that capsid-modified rAAV2 viral particles encapsidating a rAAV nucleic acid vector containing the truncated calcitonin promoter were capable of transducing MTC cells in vivo. These results demonstrate that such rAAV particles and rAAV nucleic acid vectors are useful, e.g., to target MTC cells both in vitro and in vivo.

In some embodiments, aspects of the description relate to a nucleic acid comprising an expression construct containing a truncated calcitonin promoter operably linked to a coding sequence of a gene of interest. In some embodiments, the expression construct is flanked on each side by an inverted terminal repeat sequence. In some embodiments, the truncated calcitonin promoter comprises a proximal promoter region of a calcitonin gene having the coordinates −185 to +125, relative to the transcription start site of a calcitonin coding sequence of the calcitonin gene, and a tissue-specific enhancer region of the calcitonin gene having the coordinates −1080 to −860, relative to the transcription start site of the calcitonin coding sequence. In some embodiments, the truncated calcitonin promoter comprises the sequence of SEQ ID NO: 1. In some embodiments, the gene of interest is a selected gene that is therapeutically useful for treating cancer or other conditions (e.g., medullary thyroid cancer or other medullary thyroid condition). In some embodiments, the nucleic acid is a recombinant adeno-associated virus (rAAV) vector. In some embodiments, the nucleic acid is a single-stranded or self-complementary rAAV nucleic acid vector. In some embodiments, the gene of interest is CYP2B6.

In some embodiments, aspects of the description relate to a recombinant adeno-associated virus (rAAV) particle comprising a nucleic acid described herein. In some embodiments, the rAAV particle is an rAAV2 particle. In some embodiments, the rAAV2 particle comprises a modified capsid protein comprising a non-native amino acid substitution at a position that corresponds to a surface-exposed amino acid in a wild-type AAV2 capsid protein.

In some embodiments of an rAAV particle, the non-native amino acid substitution is selected from:

(a) a non-tyrosine amino acid at Y730, (b) a non-serine amino acid at S662, (c) a non-threonine amino acid at T491, (d) a non-serine amino acid at S662 and a non-threonine amino acid at T491, (e) a non-tyrosine amino acid at Y444, a non-tyrosine amino acid at Y500, and a non-tyrosine amino acid at Y730, or (f) a non-tyrosine amino acid at Y444, a non-tyrosine amino acid at Y500, a non-tyrosine amino acid at Y730 and a non-threonine amino acid at T491.

In some embodiments of an rAAV particle, the non-native amino acid substitution is selected from:

(a) Y730F, (b) S662V, (c) T491V, (d) S662V and T491V, (e) Y444F, Y500F, and Y730F, or (f) Y444F, Y500F, Y730F and T491V.

In some embodiments of an rAAV particle, the non-native amino acid substitution is selected from (a) Y730F and (e) Y444F, Y500F, and Y730F.

In some embodiments, aspects of the description provide a composition that includes a plurality of rAAV particles described herein. In some embodiments, a composition includes a pharmaceutically acceptable carrier.

In some embodiments, aspects of the description provide a method of delivering a nucleic acid to a medullary thyroid carcinoma cell by administering an rAAV particle or composition described herein to a medullary thyroid carcinoma cell. In some embodiments, the cell is a cell in a subject. In some embodiments, a method of treating or assisting in the treatment of medullary thyroid carcinoma includes administering an rAAV particle or composition described herein to a subject having medullary thyroid carcinoma.

In some embodiments, a method of delivering a nucleic acid to a medullary thyroid carcinoma cell includes administering to a medullary thyroid carcinoma cell a rAAV2 particle comprising:

(a) a modified capsid protein comprising a non-native amino acid substitution at a position that corresponds to a surface-exposed amino acid in a wild-type AAV2 capsid protein; and (b) a nucleic acid comprising an expression construct containing a promoter operably linked to a coding sequence of a gene of interest.

In some embodiments, the non-native amino acid substitution is selected from:

(a) a non-tyrosine amino acid at Y730, (b) a non-serine amino acid at S662, (c) a non-threonine amino acid at T491, (d) a non-serine amino acid at S662 and a non-threonine amino acid at T491, (e) a non-tyrosine amino acid at Y444, a non-tyrosine amino acid at Y500, and a non-tyrosine amino acid at Y730, or (f) a non-tyrosine amino acid at Y444, a non-tyrosine amino acid at Y500, a non-tyrosine amino acid at Y730 and a non-threonine amino acid at T491.

In some embodiments, the non-native amino acid substitution is selected from:

(a) Y730F, (b) S662V, (c) T491V, (d) S662V and T491V, (e) Y444F, Y500F, and Y730F, or (f) Y444F, Y500F, Y730F and T491V.

In some embodiments, the non-native amino acid substitution is selected from (a) Y730F and (e) Y444F, Y500F, and Y730F.

These and other aspects are described in more detail herein.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

(FIG. 1A) Quantification of transduction efficiency of wild-type AAV2 in HeLa vs. TT cells as measured by eGFP expression. (FIG. 1B) Quantification of transduction efficiency of capsid mutants compared to wild-type AAV2 in the TT cell line. All cells were analyzed at 48 h post-transduction at MOI of $2\times10^3$ vector genomes per cell. P<0.01 and *P<0.001 compared to wild-type AAV2 expression.

(FIG. 2A) Schematic representation of the calcitonin promoter with enhancer and proximal promoter regions highlighted. The shaded area downstream represents the location of the transgene expressed. "E", "P", and "PS" denote sequence areas used in subsequent experiments. (FIG. 2B) Relative luciferase expression levels of the full-length calcitonin promoter from −1738 to +125 in MTC cell line TT, and 7 non-MTC cell lines. The data are shown as percentage of Firefly luciferase relative to co-transfected SV40-*renilla* expression. (FIG. 2C) Evaluation of expression from truncated promoter and enhancer regions of the calcitonin promoter compared to the full length promoter. Proximal promoter regions P encompass −185 to +125, PS −140 to +125, and enhancer region −860 to −1080, with numbers representing single or repeated promoter or enhancer regions. n=3 for all experiments. *P<0.001 TT vs. other cell lines, P<0.01 compared to full-length calcitonin promoter.

(FIG. 3A) Representative eGFP expression images of cell lines. (FIG. 3B) Quantification of eGFP-positive cells (n=4). (FIGS. 3C-3D) Flow cytometry images of infected cells— black represents untreated, grey mock infected, and green eGFP infected cells. All analyses were done at 48 hours post-transduction at an MOI of $2\times10^3$ vector genomes per cell. *P<0.05, P<0.01, *P<0.001.

FIGS. 4A, 4B, 4C, and 4D are a series of photographs that show histological analysis of rAAV-injected MTC xenograft tumors. (FIG. 4A) H&E staining of tumor tissue demonstrated MTC morphology and vascularization of tumors. (FIG. 4B) Strong calcitonin expression was seen within the C cells of the MTC xenografts. (FIG. 4C) Positive immunohistochemical staining was observed in dsAAV2-Y730E-CP1.E2 injected tumors. (FIG. 4D) Expression of eGFP was absent in IgG controls. Scale bars represent 50 μm.

FIG. 5 is a graph showing relative change in GFP expression in cells infected with wild-type rAAV2, rAAV2 (Y730F), rAAV2 (S662V), rAAV2(T491V), rAAV2 (S662V+T491V), rAAV2(Y444F+Y500F+Y730F) (M3), and rAAV2(M3+T491V).

DETAILED DESCRIPTION OF THE INVENTION

Figure 1A:
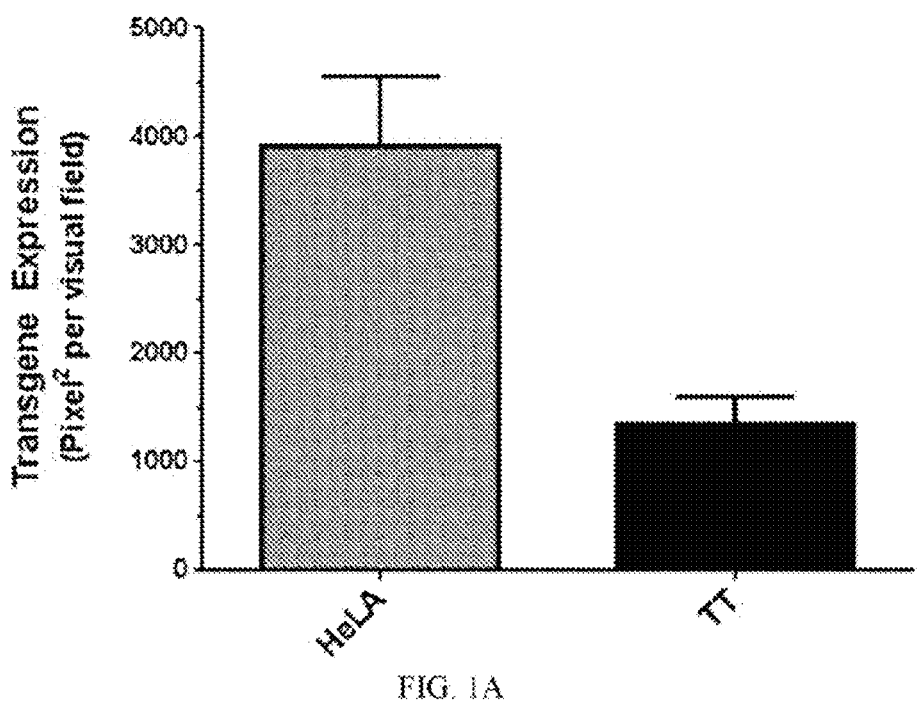
FIGS. 1A and 1B are graphs showing evaluation of wild-type (WT) and capsid mutant AAV2 expression in the MTC cell line TT.

Provided herein are nucleic acids, recombinant adeno-associated virus (rAAV) particles, compositions, and methods related in part to gene therapy for medullary thyroid carcinoma.

Medullary thyroid carcinomas (MTC) originate in parafollicular, or C cells, of the thyroid. MTC often presents with metastatic disease and once metastasized, are incurable. There remains a need for therapeutics for MTC.

The study described herein was used to determine if recombinant adeno-associated viral vectors (rAAV) could specifically target MTC. It was postulated that gene therapeutic approaches could target MTC cells. First, rAAV viral particles capable of targeting MTC cells were identified. In the MTC cell line TT, rAAV2 with mutated surface amino acids within the capsid proteins showed improved transduction compared to wild-type virus. Next, a truncated calcitonin promoter was used to achieve tissue-specific expression. Transgene expression from the truncated calcitonin promoter was specific to MTC cells compared to other non-thyroid cell lines in vitro. Finally, expression of a capsid-modified rAAV viral particle containing a nucleic acid vector comprising a truncated calcitonin promoter was evaluated in vivo in a mouse xenograft model of MTC. By assessing transduction in vivo, eGFP expression was observed following intratumor rAAV injections in a human MTC xenograft model. The results of the study described herein demonstrate that modified rAAV particles (e.g., rAAV2 containing one or more mutations in a surface-exposed residue in the capsid protein), optionally combined with a truncated calcitonin promoter, can be used to selectively target MTC.

Recombinant Adeno-Associated Virus (rAAV) Particles and Nucleic Acids

Aspects of the disclosure relate to recombinant AAV (rAAV) particles and nucleic acids.

In some embodiments, a nucleic acid is provided, the nucleic acid comprising an expression construct containing a truncated calcitonin promoter operably linked to a coding sequence of a gene of interest. As used herein, a truncated calcitonin promoter is a promoter that comprises enhancer and/or basal promoter elements from a calcitonin promoter but is not a full-length calcitonin promoter. In some embodiments, the truncated calcitonin promoter is less than 1.6 kb in length, less than 1.5 kb in length, less than 1.4 kb in length, less than 1.3 kb in length, less than 1.2 kb in length, less than 1.1 kb in length, less than 1 kb in length, or less than 900 bp in length. In some embodiments, the expression construct is flanked on each side by an inverted terminal repeat sequence. In some embodiments, the truncated calcitonin promoter is a human truncated calcitonin promoter.

In some embodiments, the truncated calcitonin promoter comprises a proximal promoter region of a calcitonin gene having the coordinates −185 to +125, relative to the transcription start site of a calcitonin coding sequence of the calcitonin gene, and a tissue-specific enhancer region of the calcitonin gene having the coordinates −1080 to −860, relative to the transcription start site of the calcitonin coding sequence.

Full Calcitonin Upstream Region (SEQ ID NO: 3)
```
gatccggggctcattgtgcccaagatccgccatcca agccctgctctgcgcgcagcttgcctgtttcacgc tctgcgcctgacacgcgccggtgtcctcccgggcc agttccagtcccgggtcctgtggccgccctgccgg cggaccctgcggagagcgagtcttagatacccagt ccccagccccgagttgttattccctcgctgtagtt aagaaggaggagatcaattaagggcatcttagaag ttaggcgttcccgctgcctcctttgagcacggagg ccaccaacccctaggggggaagagatgtagcgcga ggcaggggtgtcgtgctaagaaatttcgacgcttc tggggactgaggacaaaggtgcggacacgaccccg gggtacctggagttccgtgactcgcgccacggacg gcacacctaggggctaatttctgctctgcctcaaa gaacctcaagctagagtccttgcctccgcccacag ccccgggatgccgctgctgcgctcaccgcacaggc agcgcccggaccggctgcagcagatcgcgcgctgc gcgttccaccgggagatggtggagacgctgaaaag cttctttcttgccactctggacgctgtgggcggca agcgccttagtccctacctctgctgagctgaacgc tcaggcacagtggaactgaaacccggttctgcggg atgtgagagctgttgaggtcacgcgtaattgggtg tgatggagggcgcctgttcgtgatgtgtgcaggtt tgatgcaagcaggtcatcgtcgtgcgagtgtgtgg atgcgaccgcccgagagactcggaggcaggcttgg gacacgtttgagtgaacacctcaggatactcttct ggccagtatctgtttttttagtgtctgtgattcaga gtgggcacatgttgggagacagtaatgggtttggg tgtgtgtaaatgagtgtgtgaccggaagcgagtgtga gcttgatctaggcagggaccacacagcactgtcac acctgcctgctctttagtagaggactgaagtgcgg gggtgggggtacggggccggaatagaatgtctctg ggacatcttggcaaacagcagccggaagcaaaggg
```

-continued
```
gcagctgtgcaaacggctcaggcaggtgatggatg gcagggtaggaaggggggaggtccagaggtctggat ggaggcttccgcatctgtaccttgcaactcacccc tcaggcccagcaggtcatcggcccccctcctcacac atgtaatggatctgaagagtaccccgggacagtcc ggggagatggagattcggaaagtatccatggagat cttacagaatccctgtgcggaccaggaaactctt gtagatccctgcctatctgaggcccaggcgctggg ctgtttctcacaatattccttcaagatgagattgt ggtccccatttcaaagatgagtacactgagcctct gtgaagttacttgcccatgatcacacaaccaggaa ttgggccaactgtaattgaactcctgtctaacaaa gttcttgctcccagctccgtctcttgtttcccacg agccctggccctctgtgggtaataccagctactgg agtcagatttcttgggcccagaacccacccttagg ggcattaacctttaaaatctcacttgggcaggggt ctgggatcagagttggaagagtccctacaatcctg gaccctttccgccaaatcgtgaaaccaggggtgga gtggggcgagggttcaaaaccaggccggactgaga ggtgaaattcaccatgacgtcaaactgccctcaaa ttcccgctcactttaagggcgttacttgttggtgc ccccaccatcccccaccattccatcaatgacctc aatgcaaatacaagtgggacggtcctgctggatcc tccaggttctggaagcatgagggtgacgcaaccca ggggcaaaggacccctccgcccattggttgctgtg cactggcggaactttcccgacccacagcggcggga ataagagcagtcgctggcgctgggaggcatcagag acactgcccagcccaagtgtcgccgccgcttccac agggctctggctggacgccgccgccgccgctgcca ccgcctctgatccaagccacctcccgccaggtgag ccccgagatcctggctcaggtatatgtctctccct cc
```
atc = transcription start site
italicized text = P1
Underlined text = E In some embodiments, the truncated calcitonin promoter comprises or consists of the sequence of SEQ ID NO: 1. In some embodiments, the truncated calcitonin promoter comprises the sequence of SEQ ID NO: 1 and is no more than 1000, 900, or 800 nucleotides in length. In some embodiments, the truncated calcitonin promoter comprises a sequence that is at least 80%, 85%, 90%, 95%, 96%, 97%, 98%, 99%, or 99.5% identical to the sequence of SEQ ID NO: 1 and optionally has at least 80%, 85%, 90%, 95%, 96%, 97%, 98%, 99%, 100%, or more of the activity (e.g., promotion of transcription of a gene, such as in a medullary thyroid carcinoma cell) compared to a truncated calcitonin promoter having the sequence of SEQ ID NO: 1:

(SEQ ID NO: 1)
```
TTCCATCAATGACCTCAATGCAAATACAAGTGGGAC

GGTCCTGCTGGATCCTCCAGGTTCTGGAAGCATGA

GGGTGACGCAACCCAGGGGCAAAGGACCCCTCCGC

CCATTGGTTGCTGTGCACTGGCGGAACTTTCCCGA

CCCACAGCGGCGGGAATAAGAGCAGTCGCTGGCGC

TGGGAGGCATCAGAGACACTGCCCAGCCCAAGTGT

CGCCGCCGCTTCCACAGGGCTCTGGCTGGACGCCG

CCGCCGCCGCTGCCACCGCCTCTGATCCAAGCCAC

CTCCCGCCA
```

The coding sequence of a gene of interest may be any coding sequence of any gene that is appropriate for use in gene therapy. In some embodiments, the gene of interest is a gene that encodes a cytochrome protein. In some embodiments, the gene of interest is a CYP2B6 gene (e.g., a human CYP2B6 gene), which encodes the protein Cytochrome P450 2B6 (e.g., human Cytochrome P450 2B6).

```
An example of a CYP2B6 cDNA
sequence is as follows:
                              (SEQ ID NO: 4)
caggaccatggaactcagcgtcctcctcttccttg cactcctcacaggactcttgctactcctggttcag cgccaccctaacacccatgaccgcctcccaccagg gccccgccctctgcccttttgggaaaccttctgc agatggatagaagaggcctactcaaatcctttctg aggttccgagagaaatatggggacgtcttcacggt acacctgggaccgaggcccgtggtcatgctgtgtg gagtagaggccatacgggaggcccttgtggacaag gctgaggccttctctggccggggaaaaatcgccat ggtcgaccattcttccggggatatggtgtgatct ttgccaatggaaaccgctggaaggtgcttcggcga ttctctgtgaccactatgagggacttcgggatggg aaagcggagtgtggaggagcggattcaggaggagg ctcagtgtctgatagaggagcttcggaaatccaag ggggccctcatggaccccaccttcctcttccagtc cattaccgccaacatcatctgctccatcgtctttg gaaaacgattccactaccaagatcaagagttcctg aagatgctgaacttgttctaccagacttttttcact catcagctctgtattcggccagctgtttgagctct tctctggcttcttgaaatactttcctggggcacac aggcaagtttacaaaaacctgcaggaaatcaatgc ttacattggccacagtgtggagaagcaccgtgaaa ccctggacccccagcgcccccaaggacctcatcgac acctacctgctccacatggaaaaagagaaatccaa
```

-continued
```
cgcacacagtgaattcagccaccagaacctcaacc tcaacacgctctcgctcttctttgctggcactgag accaccagcaccactctccgctacggcttcctgct catgctcaaataccctcatgttgcagagagagtct acaggagattgaacaggtgattggcccacatcgc cctccagagcttcatgaccgagccaaaatgccata cacagaggcagtcatctatgagattcagagattttt ccgaccttctccccatgggtgtgccccacattgtc acccaacacaccagcttccgagggtacatcatccc caaggacacagaagtatttctcatcctgagcactg ctctccatgacccacactactttgaaaaaccagac gccttcaatcctgaccactttctggatgccaatgg ggcactgaaaaagactgaagcttttatccccttct ccttagggaagcggatttgtcttggtgaaggcatc gcccgtgcggaattgttcctcttcttcaccaccat cctccagaacttctccatggccagccccgtggccc cagaagacatcgatctgacaccccaggagtgtggt gtgggcaaaatacccccaacataccagatccgctt cctgccccgctgaaggggctgagggaaggggtca aaggattccagggtcatttcagtgttccccgcctc tgttagacaatggctctgactcccccgcaacttcc ttgcctctgagagaccttgctacaagccagcttcc ttcccctccatggcaccagttgtctgaggtcacat tgcaagtgagtgcaggagtgagattatcgaaaatt ataatatacaaaatcatatatatatatatgttctt gttttttgagacagagtctcacactgttgcccagg ctggagtgcagtggcgtgatctcggctcactgcaa cctccaccccgggatcaagcaactctcctgcct cagcctccctagtagctgggattacaggcatgcac taccacgcttggctaattttttgttatttttagtag agatgggg tttcactgtgtaggccaggctggtctc gaactcctgaactcaagtgattcacccaccttagc ctcccaaagtgctgggattacaggcgtgagtcacc gtgcccagccatgtatatatataattttaaaaatt aagctgaaattcacataacataaaattagctgttt taaagttgtaaaatttagtggcgtgtggttcattc acaaagctgtacaaccaccaccatctagttccaaa cattttctttttttctgagatggagtctcactctg tcacccaggttcgagttcagtggtgccatctcttg tccactgcaacctccacatcctgggttcaagtgat tctcctgcctcagcctctggaggagctggtatcac
```

-continued

```
aggcgtcccccaccacgcctggctaaattttgtat ttttaggtggtcttgaactcctgatgtcaggtgat tctcctagctccaaatgtttcattatctctcccc caacaaacccatacctatcaagctgtcactcccc atacccattctcttttcatctcggcccctgtca atctggttttgtcactatggacttaccaattctg aatatttcccataaacagaatcatacaatatttga ttttttttttttttttttgaaactaagccttgctc tgtctcccaggctggagtgctatggtgcaattttt gttcactgcaacctctgccttccaagatcaagaga ttctccagtctcagctcccaagtagctgggattac aggcatgtactaccatgcctggctaattttcttgt agttttagtagggacatgttggccaggctggtggt gagctcctggcctcaggtgatccacccacctcagt gttccaaagtgctgatattacaggcataatatgtg atcttttgtgtctggttgctttcatgttgaattgc tattttgaggttcatgcctgttgtagaccacagt cacacactgctgtagtcttccccagtcctcattcc cagctgcctcttcctactgcttccgtctatcaaaa agccccttggcccaggttccctgagctgtgggat tctgcactggtgctttggattccctgatatgttcc ttcaaatctgctgagaattaaattaaacatcttct aaagcctgacctccccacgtc
```

In some embodiments, the gene of interest is a detectable reporter gene. Exemplary detectable reporter genes include genes encoding a fluorescent protein (e.g., GFP, YFP, RFP, CFP, BFP and variants thereof), luciferase, β-galactosidase, chloramphenicol acetyltransferase and/or alkaline phosphatase.

In some embodiments, the expression construct comprises one or more regions comprising a sequence that facilitates expression of the coding sequence of the gene of interest, e.g., expression control sequences operably linked to the coding sequence. Non-limiting examples of expression control sequences include promoters, insulators, silencers, response elements, introns, enhancers, initiation sites, termination signals, and poly(A) tails. Any combination of such control sequences is contemplated herein (e.g., a promoter and an enhancer). In some embodiments, the promoter is a truncated calcitonin promoter as described herein.

In some embodiments, the nucleic acid is a plasmid (e.g., a circular nucleic acid comprising one or more of an origin of replication, a selectable marker, and a reporter gene). In some embodiments, a nucleic acid described herein, such as a plasmid, may also contain marker or reporter genes, e.g., LacZ or a fluorescent protein, and an origin of replication. In some embodiments, the plasmid is transfected into a producer cell that produces AAV particles containing the expression construct.

In some embodiments, the nucleic acid is a nucleic acid vector such as a recombinant adeno-associated virus (rAAV)

vector. Exemplary rAAV nucleic acid vectors useful according to the disclosure include single-stranded (ss) or self-complementary (sc) AAV nucleic acid vectors.

In some embodiments, a recombinant rAAV particle comprises a nucleic acid vector, such as a single-stranded (ss) or self-complementary (sc) AAV nucleic acid vector. In some embodiments, the nucleic acid vector contains an expression construct as described herein and one or more regions comprising inverted terminal repeat (ITR) sequences (e.g., wild-type ITR sequences or engineered ITR sequences) flanking the expression construct. In some embodiments, the nucleic acid is encapsidated by a viral capsid.

Accordingly, in some embodiments, a rAAV particle comprises a viral capsid and a nucleic acid vector as described herein, which is encapsidated by the viral capsid. In some embodiments, the viral capsid comprises 60 capsid protein subunits comprising VP1, VP2 and VP3. In some embodiments, the VP1, VP2, and VP3 subunits are present in the capsid at a ratio of approximately 1:1:10, respectively.

The ITR sequences of a nucleic acid or nucleic acid vector described herein can be derived from any AAV serotype (e.g., 1, 2, 3, 4, 5, 6, 7, 8, 9, or 10) or can be derived from more than one serotype. In some embodiments of the nucleic acid or nucleic acid vector provided herein, the ITR sequences are derived from AAV2. ITR sequences and plasmids containing ITR sequences are known in the art and commercially available (see, e.g., products and services available from Vector Biolabs, Philadelphia, PA; Cellbiolabs, San Diego, CA; Agilent Technologies, Santa Clara, Ca; and Addgene, Cambridge, MA; and Gene delivery to skeletal muscle results in sustained expression and systemic delivery of a therapeutic protein. Kessler P D, Podsakoff G M, Chen X, McQuiston S A, Colosi P C, Matelis L A, Kurtzman G J, Byrne B J. Proc Natl Acad Sci USA. 1996 Nov. 26; 93(24):14082-7; and Curtis A. Machida. Methods in Molecular Medicine™. Viral Vectors for Gene Therapy Methods and Protocols. 10.1385/1-59259-304-6:201 © Humana Press Inc. 2003. Chapter 10. Targeted Integration by Adeno-Associated Virus. Matthew D. Weitzman, Samuel M. Young Jr., Toni Cathomen and Richard Jude Samulski; U.S. Pat. Nos. 5,139,941 and 5,962,313, all of which are incorporated herein by reference). An exemplary AAV2 ITR sequence is shown below.

```
                                    (SEQ ID NO: 5)
TTGGCCACTCCCTCTCTGCGCGCTCGCTCGCTCAC

TGAGGCCGGGCGACCAAAGGTCGCCCGACGCCCGG

GCTTTGCCCGGGCGGCCTCAGTGAGCGAGCGAGCG

CGCAGAGAGGGAGTGGCCAACTCCATCACTAGGGG

TTCCT
```

In some embodiments, the expression construct is no more than 7 kilobases, no more than 6 kilobases, no more than 5 kilobases, no more than 4 kilobases, or no more than 3 kilobases in size. In some embodiments, the expression construct is between 4 and 7 kilobases in size.

The rAAV particle may be of any AAV serotype (e.g., 1, 2, 3, 4, 5, 6, 7, 8, 9, or 10), including any derivative (including non-naturally occurring variants of a serotype) or pseudotype. In some embodiments, the rAAV particle is an rAAV2 particle. Non-limiting examples of derivatives and pseudotypes include AAV2-AAV3 hybrid, AAVrh.10, AAVhu.14, AAV3a/3b, AAVrh32.33, AAV-HSC15, AAV-HSC17, AAVhu.37, AAVrh.8, CHt-P6, AAV2.5, AAV6.2, AAV2i8, AAV-HSC15/17, AAVM41, AAV9.45, AAV6 (Y445F/Y731F), AAV2.5T, AAV-HAE1/2, AAV clone 32/83, AAVShH10, AAV2 (Y→F), AAV8 (Y733F), AAV2.15, AAV2.4, AAVM41, and AAVr3.45. Such AAV serotypes and derivatives/pseudotypes, and methods of producing such derivatives/pseudotypes are known in the art (see, e.g., Mol Ther. 2012 April; 20(4):699-708. doi: 10.1038/mt.2011.287. Epub 2012 Jan. 24. The AAV vector toolkit: poised at the clinical crossroads. Asokan Al, Schaffer D V, Samulski R J.).

In some embodiments, the rAAV particle comprises a capsid that includes modified capsid proteins (e.g., capsid proteins comprising a modified VP3 region). Methods of producing modified capsid proteins are known in the art (see, e.g., U.S Patent Publication Number US20130310443, which is incorporated herein by reference in its entirety). In some embodiments, the rAAV particle comprises a modified capsid protein comprising a non-native amino acid substitution at a position that corresponds to a surface-exposed amino acid in a wild-type capsid protein (e.g., wild-type AAV2 capsid protein, such as SEQ ID NO: 2). In some embodiments, the rAAV particle comprises a modified capsid protein comprising a non-tyrosine amino acid (e.g., a phenylalanine) at a position that corresponds to a surface-exposed tyrosine amino acid in a wild-type capsid protein, a non-threonine amino acid (e.g., a valine) at a position that corresponds to a surface-exposed threonine amino acid in the wild-type capsid protein, a non-lysine amino acid (e.g., a glutamic acid) at a position that corresponds to a surface-exposed lysine amino acid in the wild-type capsid protein, a non-serine amino acid (e.g., a valine) at a position that corresponds to a surface-exposed serine amino acid in the wild-type capsid protein, or a combination thereof. Exemplary surface-exposed tyrosine amino acids include positions that correspond to Y252, Y272, Y444, Y500, Y700, Y704, or Y730 of the wild-type AAV2 capsid protein. Exemplary surface-exposed serine amino acids include positions that correspond to S261, S264, S267, S276, S384, S458, S468, S492, S498, S578, S658, S662, S668, S707, or S721 of the wild-type AAV2 capsid protein. Exemplary surface-exposed threonine amino acids include positions that correspond to T251, T329, T330, T454, T455, T503, T550, T592, T581, T597, T491, T671, T659, T660, T701, T713, or T716 of the wild-type AAV2 capsid protein. Exemplary surface-exposed lysine amino acids include positions that correspond to K258, K321, K459, K490, K507, K527, K572, K532, K544, K549, K556, K649, K655, K665, or K706 of the wild-type AAV2 capsid protein.

An exemplary, non-limiting wild-type AAV2 capsid protein sequence is provided below.

Exemplary Wild-Type AAV2 Capsid Protein

```
                                    (SEQ ID NO: 2)
  1 MAADGYLPDW LEDTLSEGIR QWWKLKPGPP

PPKPAERHKD DSRGLVLPGY

51 KYLGPFNGLD KGEPVNEADA AALEHDKAYD

RQLDSGDNPY LKYNHADAEF

101 QERLKEDTSF GGNLGRAVFQ AKKRVLEPLG

LVEEPVKTAP GKKRPVEHSP

151 VEPDSSSGTG KAGQQPARKR LNFGQTGDAD

SVPDPQPLGQ PPAAPSGLGT
```

-continued

```
201 NTMATGSGAP MADNNEGADG VGNSSGNWHC

DSTWMGDRVI TTSTRTWALP

251 TYNNHLYKQI SSQSGASNDN HYFGYSTPWG

YFDFNRFHCH FSPRDWQRLI

301 NNNWGFRPKR LNFKLFNIQV KEVTQNDGTT

TIANNLTSTV QVFTDSEYQL

351 PYVLGSAHQG CLPPFPADVF MVPQYGYLTL

NNGSQAVGRS SFYCLEYFPS

401 QMLRTGNNFT FSYTFEDVPF HSSYAHSQSL

DRLMNPLIDQ YLYYLSRTNT

451 PSGTTTQSRL QFSQAGASDI RDQSRNWLPG

PCYRQQRVSK TSADNNNSEY

501 SWTGATKYHL NGRDSLVNPG PAMASHKDDE

EKFFPQSGVL IFGKQGSEKT

551 NVDIEKVMIT DEEEIRTTNP VATEQYGSVS

TNLQRGNRQA ATADVNTQGV

601 LPGMVWQDRD VYLQGPIWAK IPHTDGHFHP

SPLMGGFGLK HPPPQILIKN

651 TPVPANPSTT FSAAKFASFI TQYSTGQVSV

EIEWELQKEN SKRWNPEIQY

701 TSNYNKSVNV DFTVDTNGVY SEPRPIGTRY

LTRNL*
```

In some embodiments, the non-native amino acid substitution in the capsid protein is a non-native amino acid substitution in a AAV2 capsid protein selected from:

(a) a non-tyrosine amino acid at Y730, (b) a non-serine amino acid at S662, (c) a non-threonine amino acid at T491, (d) a non-serine amino acid at S662 and a non-threonine amino acid at T491, (e) a non-tyrosine amino acid at Y444, a non-tyrosine amino acid at Y500, and a non-tyrosine amino acid at Y730, or (f) a non-tyrosine amino acid at Y444, a non-tyrosine amino acid at Y500, a non-tyrosine amino acid at Y730 and a non-threonine amino acid at T491.

In some embodiments, the non-native amino acid substitution in the capsid protein is a non-native amino acid substitution in a AAV2 capsid protein selected from:

(a) Y730F, (b) S662V, (c) T491V, (d) S662V and T491V, (e) Y444F, Y500F, and Y730F, or (f) Y444F, Y500F, Y730F and T491V. In some embodiments, the non-native amino acid substitution is Y730F in an AAV2 capsid protein. In some embodiments, the non-native amino acid substitution is S662V in an AAV2 capsid protein. In some embodiments, the non-native amino acid substitution is T491V in an AAV2 capsid protein. In some embodiments, the non-native amino acid substitution is S662V and T491V in an AAV2 capsid protein. In some embodiments, the non-native amino acid substitution is Y444F, Y500F, and Y730F in an AAV2 capsid protein. In some embodiments, the non-native amino acid substitution is Y444F, Y500F, Y730F and T491V in an AAV2 capsid protein.

Methods of producing rAAV particles and nucleic acid vectors are also known in the art and commercially available (see, e.g., Zolotukhin et al. Production and purification of serotype 1, 2, and 5 recombinant adeno-associated viral vectors. Methods 28 (2002) 158-167; and U.S. Patent Publication Numbers US20070015238 and US20120322861, which are incorporated herein by reference; and plasmids and kits available from ATCC and Cell Biolabs, Inc.). For example, the nucleic acid vector (e.g., as a plasmid) may be combined with one or more helper plasmids, e.g., that contain a rep gene (e.g., encoding Rep78, Rep68, Rep52 and Rep40) and a cap gene (encoding VP1, VP2, and VP3), and transfected into a producer cell line such that the rAAV particle can be packaged and subsequently purified.

In some embodiments, the one or more helper plasmids includes a first helper plasmid comprising a rep gene and a cap gene and a second helper plasmid comprising other genes that assist in AAV production, such as a Ela gene, a E1b gene, a E4 gene, a E2a gene, and a VA gene. In some embodiments, the rep gene is a rep gene derived from AAV2 and the cap gene is derived from AAV5. Helper plasmids, and methods of making such plasmids, are known in the art and commercially available (see, e.g., pDM, pDG, pDP1rs, pDP2rs, pDP3rs, pDP4rs, pDP5rs, pDP6rs, pDG(R484E/R585E), and pDP8.ape plasmids from PlasmidFactory, Bielefeld, Germany; other products and services available from Vector Biolabs, Philadelphia, PA; Cellbiolabs, San Diego, CA; Agilent Technologies, Santa Clara, Ca; and Addgene, Cambridge, MA; pxx6; Grimm et al. (1998), Novel Tools for Production and Purification of Recombinant Adenoassociated Virus Vectors, Human Gene Therapy, Vol. 9, 2745-2760; Kern, A. et al. (2003), Identification of a Heparin-Binding Motif on Adeno-Associated Virus Type 2 Capsids, Journal of Virology, Vol. 77, 11072-11081; Grimm et al. (2003), Helper Virus-Free, Optically Controllable, and Two-Plasmid-Based Production of Adeno-associated Virus Vectors of Serotypes 1 to 6, Molecular Therapy, Vol. 7, 839-850; Kronenberg et al. (2005), A Conformational Change in the Adeno-Associated Virus Type 2 Capsid Leads to the Exposure of Hidden VP1 N Termini, Journal of Virology, Vol. 79, 5296-5303; and Moullier, P. and Snyder, R. O. (2008), International efforts for recombinant adeno-associated viral vector reference standards, Molecular Therapy, Vol. 16, 1185-1188).

An exemplary, non-limiting, rAAV particle production method is described next. One or more helper plasmids are produced or obtained, which comprise rep and cap ORFs for the desired AAV serotype and the adenoviral VA, E2A (DBP), and E4 genes under the transcriptional control of their native promoters. HEK293 cells (available from ATCC®) are transfected via CaPO4-mediated transfection, lipids or polymeric molecules such as Polyethylenimine (PEI) with the helper plasmid(s) and a plasmid containing a nucleic acid vector described herein. Alternatively, in another example, Sf9-based producer stable cell lines are infected with a single recombinant baculovirus containing the nucleic acid vector. As a further alternative, in another example HEK293 or BHK cell lines are infected with a HSV containing the nucleic acid vector and optionally one or more helper HSVs containing rep and cap ORFs as described herein and the adenoviral VA, E2A (DBP), and E4 genes under the transcriptional control of their native promoters. The HEK293, BHK, or Sf9 cells are then incubated for at least 60 hours to allow for rAAV particle production. The rAAV particles can then be purified using any method known in the art or described herein, e.g., by iodixanol step gradient, CsCl gradient, chromatography, or polyethylene glycol (PEG) precipitation.

The disclosure also contemplates host cells that comprise at least one of the disclosed rAAV particles, expression constructs, or nucleic acid vectors. Such host cells include mammalian host cells, with human host cells being preferred, and may be either isolated, in cell or tissue culture. In the case of genetically modified animal models (e.g., a mouse), the transformed host cells may be comprised within the body of a non-human animal itself.

Compositions

Aspects of the disclosure relate to compositions comprising rAAV particles or nucleic acids described herein. In some embodiments, rAAV particles described herein are added to a composition, e.g., a pharmaceutical composition.

In some embodiments, the composition comprises a pharmaceutically acceptable carrier. The term "carrier" refers to a diluent, adjuvant, excipient, or vehicle with which the rAAV particle is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers. Non-limiting examples of pharmaceutically acceptable carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, polyacrylic acids, lubricating agents (such as talc, magnesium stearate, and mineral oil), wetting agents, emulsifying agents, suspending agents, preserving agents (such as methyl-, ethyl-, and propyl-hydroxy-benzoates), and pH adjusting agents (such as inorganic and organic acids and bases). Other examples of carriers include phosphate buffered saline, HEPES-buffered saline, and water for injection, any of which may be optionally combined with one or more of calcium chloride dihydrate, disodium phosphate anhydrous, magnesium chloride hexahydrate, potassium chloride, potassium dihydrogen phosphate, sodium chloride, or sucrose. Other examples of carriers that might be used include saline (e.g., sterilized, pyrogen-free saline), saline buffers (e.g., citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. USP grade carriers and excipients are particularly useful for delivery of rAAV particles to human subjects. Such compositions may further optionally comprise a liposome, a lipid, a lipid complex, a microsphere, a microparticle, a nanosphere, or a nanoparticle, or may be otherwise formulated for administration to the cells, tissues, organs, or body of a subject in need thereof. Methods for making such compositions are well known and can be found in, for example, Remington: The Science and Practice of Pharmacy, $22^{nd}$ edition, Pharmaceutical Press, 2012.

Typically, such compositions may contain at least about 0.1% of the therapeutic agent (e.g., rAAV particle) or more, although the percentage of the active ingredient(s) may, of course, be varied and may conveniently be between about 1 or 2% and about 70% or 80% or more of the weight or volume of the total formulation. Naturally, the amount of therapeutic agent(s) (e.g., rAAV particle) in each therapeutically-useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In some embodiments, a composition described herein may be administered to a subject in need thereof, such as a subject having medullary thyroid carcinoma. In some embodiments, a method described herein may comprise administering a composition comprising rAAV particles as described herein to a subject in need thereof. In some embodiments, the subject is a human subject. In some embodiments, the subject has or is suspected of having a disease that may be treated with gene therapy, such as medullary thyroid carcinoma. In some embodiments, the subject has been diagnosed with medullary thyroid carcinoma.

Methods

Aspects of the disclosure relate to methods of delivering a nucleic acid to a medullary thyroid carcinoma cell. In some embodiments, the method comprises administering a rAAV particle as described herein or a composition as described herein. The method may be performed in vitro or in vivo. In some embodiments, the cell is a human medullary thyroid carcinoma cell. In some embodiments, the cell is in a subject (e.g., a human subject).

Other aspects of the disclosure relate to treatment of treating medullary thyroid carcinoma. In some embodiments, the method comprises administering a therapeutically effective amount of an rAAV particle or a composition as described herein to a subject having medullary thyroid carcinoma.

To "treat" a disease as the term is used herein, means to reduce the frequency or severity of at least one sign or symptom of a disease or disorder experienced by a subject. The compositions described above or elsewhere herein are typically administered to a subject in an effective amount, that is, an amount capable of producing a desirable result. The desirable result will depend upon the active agent being administered. For example, an effective amount of rAAV particles may be an amount of the particles that are capable of transferring an expression construct to a host organ, tissue, or cell. A therapeutically acceptable amount may be an amount that is capable of treating a disease, e.g., medullary thyroid carcinoma. As is well known in the medical and veterinary arts, dosage for any one subject depends on many factors, including the subject's size, body surface area, age, the particular composition to be administered, the active ingredient(s) in the composition, time and route of administration, general health, and other drugs being administered concurrently.

The rAAV particle or nucleic acid vector may be delivered in the form of a composition, such as a composition comprising the active ingredient, such as a rAAV particle described herein, and a pharmaceutically acceptable carrier as described herein. The rAAV particles or nucleic acid vectors may be prepared in a variety of compositions, and may also be formulated in appropriate pharmaceutical vehicles for administration to human or animal subjects.

In some embodiments, the rAAV particles administered to a subject may be provided in a composition having a concentration on the order ranging from $10^6$ to $10^{14}$ particles/ml or $10^3$ to $10^{15}$ particles/ml, or any values therebetween for either range, such as for example, about $10^6$, $10^7$, $10^8$, $10^9$, $10^{10}$, $10^{11}$, $10^{12}$, $10^{13}$, or $10^{14}$ particles/ml. In one embodiment, rAAV particles of higher than $10^{13}$ particles/ml are to be administered. In some embodiments, the number of rAAV particles administered to a subject may be on the order ranging from $10^6$ to $10^{14}$ vector genomes (vgs)/ml or $10^3$ to $10^{15}$ vgs/ml, or any values therebetween for either range, such as for example, about $10^6$, $10^7$, $10^8$, $10^9$, $10^{10}$, $10^{11}$, $10^{12}$, $10^{13}$, or $10^{14}$ vgs/ml. In one embodiment, rAAV particles of higher than $10^{13}$ vgs/ml are to be administered. The rAAV particles can be administered as a single dose, or divided into two or more administrations as may be required to achieve therapy of the particular disease or disorder being treated. In some embodiments, 0.0001 ml to 10 mls are delivered to a subject. In some embodiments, the number of rAAV particles administered to a subject may be on the order ranging from $10^6$-$10^{14}$ vg/kg, or any values therebetween, such as for example, about $10^6$, $10^7$, $10^8$, $10^9$, $10^{10}$, $10^{11}$, $10^{12}$, $10^{13}$, or $10^{14}$ vgs/kg. In some embodiments, the number of rAAV particles administered to a subject may be on the order ranging from $10^{12}$-$10^{14}$ vgs/kg.

If desired, rAAV particles may be administered in combination with other agents or therapies as well, such as, e.g., proteins or polypeptides or various pharmaceutically-active agents, including one or more systemic or topical administrations of therapeutic polypeptides, biologically active fragments, or variants thereof. In fact, there is virtually no limit to other components that may also be included, given that the additional agents do not cause a significant adverse effect upon contact with the target cells or host tissues. The rAAV particles may thus be delivered along with various other agents as required in the particular instance. In some embodiments, the other agent is cyclophosphamide. In some embodiments, rAAV particles comprising a vector encoding CYP2B6 are delivered along with (either together or separately) cyclophosphamide. Such compositions may be purified from host cells or other biological sources, or alternatively may be chemically synthesized. In some embodiments, one or more other genes that can be used to treat cancer or other conditions (e.g., medullary thyroid cancer or other medullary thyroid conditions) can be delivered (e.g., alone or along with an additional agent). In some embodiments, rAAV particles as described herein (e.g., comprising a vector encoding CYP2B6) are administered in combination with one or more of thyroidectomy, radiation therapy (e.g., with radiolabeled iodine), or thyroid hormone treatment (e.g., with a synthetic thyroid hormone such as levothyroxine).

In certain circumstances it will be desirable to deliver the rAAV particles in suitably formulated pharmaceutical compositions disclosed herein either subcutaneously, intraocularly, intravitreally, subretinally, parenterally, intravenously, intracerebro-ventricularly, intramuscularly, intrathecally, orally, intraperitoneally, by oral or nasal inhalation, or by direct injection to one or more cells, tissues, or organs. In some embodiments, the direct injection is performed ex vivo. In some embodiments, the administration is a route suitable for systemic delivery, such as by intravenous injection or infusion. The pharmaceutical forms of the rAAV particle compositions suitable for injectable use include sterile aqueous solutions or dispersions. In some embodiments, the form is sterile and fluid to the extent that easy syringability exists. In some embodiments, the form is stable under the conditions of manufacture and storage and is preserved against the contaminating action of microorganisms, such as bacteria and fungi. The carrier can be a solvent or dispersion medium containing, for example, water, saline, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. In some embodiments, rAAV particles are delivered IV, e.g., for the treatment of metastatic disease.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, intravitreal, subretinal, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by, e.g., FDA Office of Biologics standards.

Sterile injectable solutions are prepared by incorporating the rAAV particles in the required amount in the appropriate solvent with several of the other ingredients enumerated above, as required, followed by filtered sterilization or another sterilization technique. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The amount of rAAV particle or nucleic acid vector compositions and time of administration of such compositions will be within the purview of the skilled artisan having benefit of the present teachings. It is likely, however, that the administration of therapeutically-effective amounts of the disclosed compositions may be achieved by a single administration, such as for example, a single injection of sufficient numbers of infectious particles to provide therapeutic benefit to the patient undergoing such treatment. Alternatively, in some circumstances, it may be desirable to provide multiple, or successive administrations of the rAAV particle compositions, either over a relatively short, or a relatively prolonged period of time, as may be determined by the medical practitioner overseeing the administration of such compositions.

The composition may include rAAV particles, either alone, or in combination with one or more additional active ingredients, which may be obtained from natural or recombinant sources or chemically synthesized.

Toxicity and efficacy of the compositions utilized in methods of the disclosure can be determined by standard pharmaceutical procedures, using either cells in culture or experimental animals to determine the LD50 (the dose lethal to 50% of the population). The dose ratio between toxicity and efficacy is the therapeutic index and it can be expressed as the ratio LD50/ED50. Those compositions that exhibit large therapeutic indices are preferred. While those that exhibit toxic side effects may be used, care should be taken to design a delivery system that minimizes the potential damage of such side effects. The dosage of compositions as described herein lies generally within a range that includes an ED50 with little or no toxicity. The dosage may vary within this range depending upon the dosage form employed and the route of administration utilized.

Subjects

Aspects of the disclosure relate to methods for use with a subject, such as human or non-human primate subjects. Non-limiting examples of non-human primate subjects include macaques (e.g., cynomolgus or rhesus macaques), marmosets, tamarins, spider monkeys, owl monkeys, vervet monkeys, squirrel monkeys, baboons, gorillas, chimpanzees, and orangutans. In some embodiments, the subject is a human subject. Other exemplary subjects include domesticated animals such as dogs and cats; livestock such as horses, cattle, pigs, sheep, goats, and chickens; and other animals such as mice, rats, guinea pigs, and hamsters.

In some embodiments, the subject has or is suspected of having a disease that may be treated with gene therapy. In some embodiments, the subject has or is suspected of having medullary thyroid carcinoma. Medullary thyroid carcinoma (MTC) is a form of thyroid cancer which originates from C cells (parafollicular cells). MTC makes up approximately 3-4% of all thyroid cancer cases. If the MTC metastasizes, the 5-year survival rate drops to about 28%. In some embodiments, the subject has been diagnosed as having MTC. MTC can be identified by a skilled medical practitioner using methods known in the art, e.g., by measuring serum concentration of calcitonin, serum concentration of carcinoembryonic antigen (CEA), biopsy (e.g., fine needle aspiration), ultrasound, CT scan, or MRI, or any combination thereof.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1. Recombinant AAV Vector Targeting of Medullary Thyroid Carcinoma

Thyroid cancers principally develop from two types of cells within the thyroid: thyroid epithelial cells and parafollicular, or C cells (1). Epithelial cell-derived cancers, which include papillary, follicular, and anaplastic carcinomas, are the most common type of thyroid cancers and account for approximately 90% of all thyroid cancer. Differentiated thyroid cancers generally have a good prognosis (2). In contrast, medullary thyroid carcinomas (MTC), which arise from C cells, account for less than 12% of thyroid cancers (3). If confined within the thyroid, MTC can be treated surgically (4). Yet most patients with MTC present with or develop metastatic disease, which is generally not curable (5-6). Tyrosine kinase inhibitors can stop MTC progression, but are not curative (7). Thus, new approaches for the treatment of MTC are needed.

One potential novel approach for cancer treatment is through the use of gene therapy to target malignant cells using viral vectors (8). Of potential viral vectors, recombinant adeno-associated viruses (rAAVs) have recently shown to hold potential for such therapeutic approaches (9-11). There are a large number of rAAV serotypes, and different serotypes can selectively transduce different cell types (12-13). By utilizing tissue-specific promoters in these viral vectors, it is possible to achieve tissue-specific expression (14). The use of a calcitonin promoter can confer MTC specificity due to its strong and specific expression in the C cells of the thyroid (15). Viral vectors can also be utilized to incorporate genes that encode for cytotoxic factors or enzymes that convert selective agents to cytotoxic chemicals to eliminate tumor tissue (16). For example, it is possible to insert the CYP2B6 gene, which converts cyclophosphamide to acrolein and phosphamide mustard, into such vectors resulting in cell death.

It is postulated that it will be possible to develop novel gene therapy-based approaches for MTC. It is postulated that it would be possible to utilize the calcitonin promoter to achieve specific expression in MTC tissues. The study herein describes the development of rAAV vectors that transduce MTC cells in vitro and in vivo.

Materials and Methods

Cell Culture

Human MTC cell line TT, lung carcinoma cell line A549, cervical adenocarcinoma cell line HeLa, medulloblastoma cell line Daoy, breast adenocarinoma cell line MCF7, and human papillomavirus transformed kidney cell line HK-2 were obtained from American Type Culture Collection (ATCC; Manassas, Virginia, USA). The human epidermal carcinoma cell line A431 was obtained from Sigma-Aldrich. Normal thyroid epithelial cell line Nthy-ori 3-1 (SV40-immortalized) was obtained from European Collection of Cell Cultures (ECACC; Salisbury, UK). Cells were grown at 37° C. and 5% $CO_2$. All cell lines except HK-2 were grown in their recommended media supplemented with 10% fetal bovine serum (Gemini Bio-Products, West Sacramento, CA, USA). HK-2 was grown in keratinocyte serum-free media supplemented with bovine pituitary extract and human recombinant epidermal growth factor (Life Technologies).

AAV Vector Production

Recombinant AAV vectors were generated as described (17) and contained eGFP driven by the CBA promoter or calcitonin modified P1.E2 promoter. Briefly, HEK293 cells were triple transfected with polyethylenimine (PEI, linear; Polysciences, Inc., Warrington, PA, USA). Vectors were purified 72 hours post transfection by iodixanol gradient centrifugation (Sigma-Aldrich, St. Louis, MO, USA) and ion exchange column chromatography using HiTrap SP HP (GE Healthcare, Piscataway, NJ, USA). Titers were determined using a quantitative PCR assay amplifying the transgene region (18).

Construction of Plasmids

The calcitonin promoter was amplified by polymerase chain reaction (PCR) from the MTC cell line TT using the forward 5'-CAGGGGTGTCGTGCTAAGAA-3' (SEQ ID NO: 6) and reverse 5'-CCAGAATCTCGGGGCTCACCT-3' (SEQ ID NO: 7) primers corresponding to −1738 to +125 bases relative to the transcriptional start site (19). The PCR product was cloned into the pGEM vector (Promega, Madison, WI, USA) and sequenced by Sanger Sequencing at the University of Florida Interdisciplinary Center for Biotechnology Research (ICBR) DNA Sequencing Core facility.

The promoter was cloned into the pGL3 luciferase reporter vector (Promega). Synthesis of the modified calcitonin promoter sequence was performed by Life Technologies (Grand Island, NY, USA)

The chicken beta actin (CBA) promoter was removed and the P1.E2 promoter containing the proximal calcitonin promoter and duplicate enhancer sequences were cloned into the double-stranded AAV backbone expressing enhanced GFP (eGFP) using KpnI and NcoI sites.

Luciferase Assays

Transfections were performed in 96-well plates. Cells were transfected at 70% density that was equivalent to approximately $5 \times 10^3$-$10^4$ cells per well. Each well was transfected with 50 of serum-free media containing 0.1 μg of luciferase reporter plasmid, 0.1 μg pRL-SV40-*Renilla* control, and 0.3 μl of FuGene HD transfection Reagent (Promega). 48 hours post-transfection, media was removed, and cells were briefly rinsed in PBS and lysed. All experiments were analyzed using the Dual-Luciferase Reporter Assay System (Promega). Luciferase activity in each well was measured twice following addition of 100 μl of firefly luciferase substrate then 100 μl Stop & Glo *Renilla* substrate in a Biotek Synergy HT plate reader. Results are expressed as a percentage of the promoter activity compared to the SV40-*Renilla* co-transfected control.

Recombinant AAV Vector In Vitro Transduction Assays

Cells were transduced with $2 \times 10^3$ vector genomes (vgs) per cell of wild-type (WT) or capsid mutant double stranded (ds) AAV2 vectors expressing eGFP. 48 hours post-transduction, transgene expression was assessed by total area of green fluorescence pixels per visual field or by flow cytometry. For pixel analysis, 4 wells in a 96-well plate were transduced, and fluorescent images taken at 5× magnification using a Leica DM IRB fluorescence microscope. Transgene expression was assessed as the total area of green fluorescence per visual field examined for each well (pixel2). Image analysis was performed using Image J (NIH, USA). For flow cytometry, cells were plated in a 6-well plate, detached from the plates with trypsin, and suspended in PBS containing 5% fetal calf serum. Cell sorting for eGFP expression was performed on a FACS Calibur (BD Biosciences, San Jose, CA, USA) and analyzed using Cellquest Version 3.3. Each experiment was run with 10,000 cells, and untreated, mock, and AAV-transduced cells were compared. Pixel count analysis was performed in triplicate and flow cytometry in quadruplicate.

Mouse Xenograft Model of MTC and Administration of Recombinant AAV2 Mutant Vector Subcutaneous injections of $1 \times 10^7$ TT cells into the lower dorsal region were performed in 6-week-old NSG mice (Jackson Laboratories, Bar Harbor, ME, USA). Cells were suspended in PBS and mixed at a 1:1 ratio with matrigel prior to injection (BD Biosciences, San Jose, CA, USA). When tumors reached 9-10 mm in diameter, $2 \times 10^{10}$ vgs of ds AAV2 with capsid mutated Y730F containing the CBA (dsAAV2-Y730-CBA-eGFP; n=3) or the modified calcitonin CP1.E2 promoter (dsAAV2-Y730E-CP1.E2-eGFP; n=3) expressing eGFP were injected into the tumor. Mock control animals were injected with an equal volume of phosphate buffered saline (n=2). Two days after vector injection, tumors were resected.

Immunohistochemical Staining of TT MTC Xenograft Tumors for eGFP and Calcitonin Immunohistochemical (IHC) staining was performed to evaluate eGFP expression following vector injection. All tumors were sectioned in half at the site of vector injection, fixed in 4% paraformaldehyde overnight, dehydrated, and embedded in paraffin. 5 μm thick tissue sections were prepared for staining. Hematoxylin and eosin (H&E) and IHC staining was performed using a Rabbi anti-eGFP (1:100; Origene, Rockville, MD, USA) or Rabbit anti-Calcitonin (1:250; AbCam, Cambridge, MA, USA) antibody as described (19-20). All images were taken on a Zeiss Axio Vert.A1 inverted light microscope (Zeiss, Thornwood, NY, USA).

Statistical Analysis

All bar graph results are presented as mean±standard deviation. Differences between WT- and mutant virus-transduced samples and promoter activity were assessed using analysis of variance (ANOVA). Flow cytometry analysis comparing cells transduced with rAAV2-Y730F with a CBA or CP1.E2 promoter were analyzed using the t-test. P-values <0.05 were considered statistically significant.

Results

Transduction of MTC Cells by rAAV2 Capsids

Delivery of transgenes to MTC cells by rAAV2 vectors has been demonstrated in only one previous publication (11). To determine if other AAV serotypes could more efficiently transduce MTC cells, the TT cell line was transduced with rAAV1-6 in vitro. Wild-type (WT) rAAV2 capsid vectors showed significantly increased transduction compared to other serotypes as measured by eGFP expression (data not shown). When transduced with WT dsAAV2-eGFP, TT cells showed low eGFP expression that was 4-fold lower than those observed in HeLa cells (FIG. 1A)

Figure 1B:
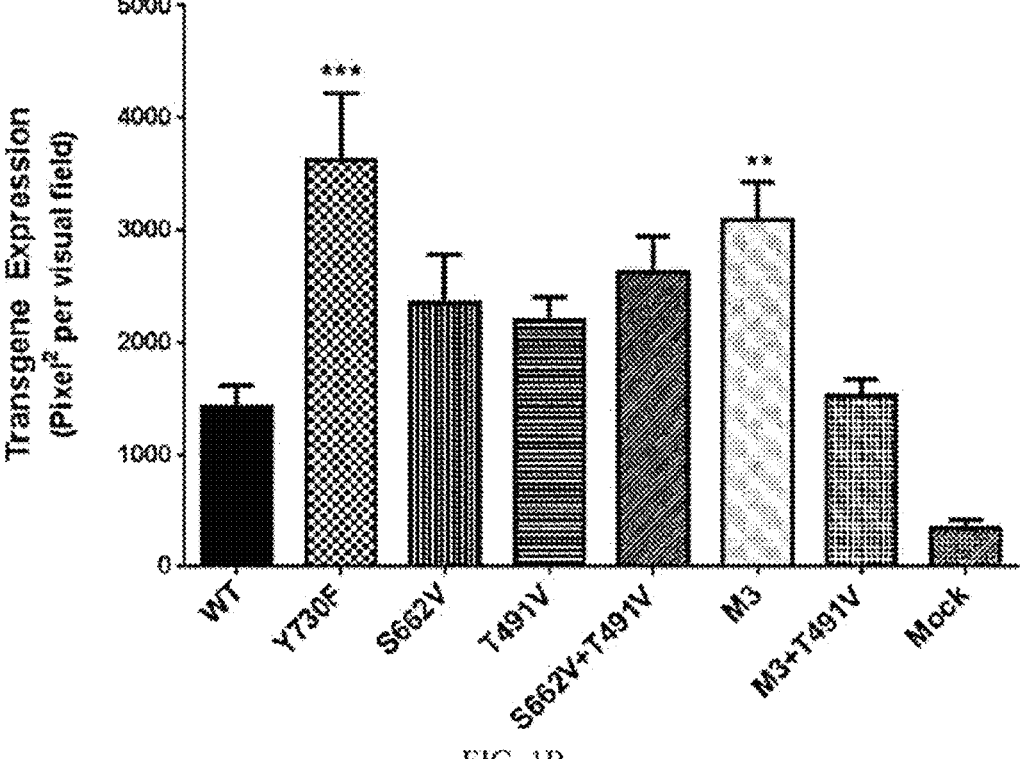

Previous work in HEK293 cells has shown that mutation of amino acids on the surface of AAV capsids increases transduction efficiency (21). To determine if capsid mutations could increase transduction by rAAV in MTC cells, WT and mutant dsAAV-eGFP-expressing vectors were transduced into TT cells, and fluorescent gene expression was compared. Variations in eGFP expression by mutant rAAV2 vectors was also compared by transducing TT cells with WT or 6 other rAAV2 capsid mutant vectors. These capsids had different mutated surface-exposed tyrosines (Y), serines (S), or threonines (T) (21). These included single amino acid substitutions: Y730F, S662V, T491V; double substitutions at S662V+T491V; triple substitutions at Y444F+Y500F+Y730F (M3); and quadruple substitutions: M3+T491V. As shown in FIG. 1B, single mutation Y730F and triple mutant M3 showed significantly increased transduction compared to WT virus in the TT cell line in vitro as measured by differences in eGFP expression. The level of transduction rivaled that seen in HeLa. These data support the hypothesis that capsid mutated dsAAV2 can improve transduction efficiency in MTC-derived cells.

A Truncated Calcitonin Promoter Region Confers C Cell Specificity In Vitro

To improve MTC-specific expression, different variants of the calcitonin promoter were examined in TT cells compared to other non-C cell-derived cells. Modified enhancer (E; −1080 to −860) and proximal promoter (P; −185 to +125) regions were synthesized with MluI, NheI, and BglII sites incorporated upstream, XbaI between the promoter and enhancer, and EcoRV and HindIII sites incorporated downstream. The proximal promoter region −185 to +125, labeled as P1, was digested with XbaI and HindIII and cloned into the pGL3 vector using the NheI and HindIII sites. A shortened version of the proximal promoter region −140 to +125, labeled PS1, was digested with BamHI and HindIII and cloned into the pGL3 vector using BglII and HindIII. The tissue-specific enhancer region −1080 to −860, labeled E1 (single) and E2 (double), were cloned upstream of the proximal promoters using the MluI and NheI sites, respectively, upstream and the XbaI downstream site. Non-limiting examples of promoter sequences include:

P1.E1

(SEQ ID NO: 8)

GATCTGAGCTTGATCTAGGCAGGGACCACACAGCA

CTGTCACACCTGCCTGCTCTTTAGTAGAGGACTGA

AGTGCGGGGGTGGGGGTACGGGGCCGGAATAGAAT

GTCTCTGGGACATCTTGGCAAACAGCAGCCGGAAG

CAAAGGGGCAGCTGTGCAAACGGCTCAGGCAGGTG

ATGGATGGCAGGGTAGGAAGGGGGAGCCAGAGGTC

TGGATGGAGGTTCTAGATTTTCCATCAATGACCTC

AATGCAAATACAAGTGGGACGGTCCTGCTGGATCC

TCCAGGTTCTGGAAGCATGAGGGTGACGCAACCCA

GGGGCAAAGGACCCCTCCGCCCATTGGTTGCTGTG

CACTGGCGGAACTTTCCCGACCCACAGCGGCGGGA

ATAAGAGCAGTCGCTGGCGCTGGGAGGCATCAGAG

ACACTGCCCAGCCCAAGTGTCGCCGCCGCTTCCAC

AGGGCTCTGGCTGGACGCCGCCGCCGCCGCTGCCA

CCGCCTCTGATCCAAGCCACCTCCCGCCACTAGTG

ATATCA

P1.E2

(SEQ ID NO: 9)

GATCTGAGCTTGATCTAGGCAGGGACCACACAGCA

CTGTCACACCTGCCTGCTCTTTAGTAGAGGACTGA

AGTGCGGGGGTGGGGGTACGGGGCCGGAATAGAAT

GTCTCTGGGACATCTTGGCAAACAGCAGCCGGAAG

CAAAGGGGCAGCTGTGCAAACGGCTCAGGCAGGTG

ATGGATGGCAGGGTAGGAAGGGGGAGCCAGAGGTC

TGGATGGAGGTTCTAGCAGATCTGAGCTTGATCTA

GGCAGGGACCACACAGCACTGTCACACCTGCCTGC

TCTTTAGTAGAGGACTGAAGTGCGGGGGTGGGGGT

ACGGGGCCGGAATAGAATGTCTCTGGGACATCTTG

GCAAACAGCAGCCGGAAGCAAAGGGGCAGCTGTGC

AAACGGCTCAGGCAGGTGATGGATGGCAGGGTAGG

AAGGGGGAGCCAGAGGTCTGGATGGAGGTTCTAGA

TTTTCCATCAATGACCTCAATGCAAATACAAGTGG

GACGGTCCTGCTGGATCCTCCAGGTTCTGGAAGCA

TGAGGGTGACGCAACCCAGGGGCAAAGGACCCCTC

CGCCCATTGGTTGCTGTGCACTGGCGGAACTTTCC

CGACCCACAGCGGCGGGAATAAGAGCAGTCGCTGG

CGCTGGGAGGCATCAGAGACACTGCCCAGCCCAAG

-continued
TGTCGCCGCCGCTTCCACAGGGCTCTGGCTGGACG

CCGCCGCCGCCGCTGCCACCGCCTCTGATCCAAGC

CACCTCCCGCCACTAGTGATATCA

PS1.E1

(SEQ ID NO: 10)
GATCTGAGCTTGATCTAGGCAGGGACCACACAGCA

CTGTCACACCTGCCTGCTCTTTAGTAGAGGACTGA

AGTGCGGGGGTGGGGGTACGGGGCCGGAATAGAAT

GTCTCTGGGACATCTTGGCAAACAGCAGCCGGAAG

CAAAGGGGCAGCTGTGCAAACGGCTCAGGCAGGTG

ATGGATGGCAGGGTAGGAAGGGGGAGCCAGAGGTC

TGGATGGAGGTTTGGATCCTCCAGGTTCTGGAAGC

ATGAGGGTGACGCAACCCAGGGGCAAAGGACCCCT

CCGCCCATTGGTTGCTGTGCACTGGCGGAACTTTC

CCGACCCACAGCGGCGGGAATAAGAGCAGTCGCTG

GCGCTGGGAGGCATCAGAGACACTGCCCAGCCCAA

GTGTCGCCGCCGCTTCCACAGGGCTCTGGCTGGAC

GCCGCCGCCGCCGCTGCCACCGCCTCTGATCCAAG

CCACCTCCCGCCACTAGTGATATCA

PS1.E2

(SEQ ID NO: 11)
GATCTGAGCTTGATCTAGGCAGGGACCACACAGCA

CTGTCACACCTGCCTGCTCTTTAGTAGAGGACTGA

AGTGCGGGGGTGGGGGTACGGGGCCGGAATAGAAT

GTCTCTGGGACATCTTGGCAAACAGCAGCCGGAAG

CAAAGGGGCAGCTGTGCAAACGGCTCAGGCAGGTG

ATGGATGGCAGGGTAGGAAGGGGGAGCCAGAGGTC

TGGATGGAGGTTCTAGCAGATCTGAGCTTGATCTA

GGCAGGGACCACACAGCACTGTCACACCTGCCTGC

TCTTTAGTAGAGGACTGAAGTGCGGGGGTGGGGGT

ACGGGGCCGGAATAGAATGTCTCTGGGACATCTTG

GCAAACAGCAGCCGGAAGCAAAGGGGCAGCTGTGC

AAACGGCTCAGGCAGGTGATGGATGGCAGGGTAGG

AAGGGGGAGCCAGAGGTCTGGATGGAGGTTTGGAT

CCTCCAGGTTCTGGAAGCATGAGGGTGACGCAACC

CAGGGGCAAAGGACCCCTCCGCCCATTGGTTGCTG

TGCACTGGCGGAACTTTCCCGACCCACAGCGGCGG

GAATAAGAGCAGTCGCTGGCGCTGGGAGGCATCAG

AGACACTGCCCAGCCCAAGTGTCGCCGCCGCTTCC

-continued
ACAGGGCTCTGGCTGGACGCCGCCGCCGCCGCTGC

CACCGCCTCTGATCCAAGCCACCTCCCGCCACTAG

TGATATCA

P1

(SEQ ID NO: 12)
TTCCATCAATGACCTCAATGCAAATACAAGTGGGA

CGGTCCTGCTGGATCCTCCAGGTTCTGGAAGCATG

AGGGTGACGCAACCCAGGGGCAAAGGACCCCTCCG

CCCATTGGTTGCTGTGCACTGGCGGAACTTTCCCG

ACCCACAGCGGCGGGAATAAGAGCAGTCGCTGGCG

CTGGGAGGCATCAGAGACACTGCCCAGCCCAAGTG

TCGCCGCCGCTTCCACAGGGCTCTGGCTGGACGCC

GCCGCCGCCGCTGCCACCGCCTCTGATCCAAGCCA

CCTCCCGCCAGGTGAGCCCCGAGATCCT

PS1

(SEQ ID NO: 13)
TGGATCCTCCAGGTTCTGGAAGCATGAGGGTGACG

CAACCCAGGGGCAAAGGACCCCTCCGCCCATTGGT

TGCTGTGCACTGGCGGAACTTTCCCGACCCACAGC

GGCGGGAATAAGAGCAGTCGCTGGCGCTGGGAGGC

ATCAGAGACACTGCCCAGCCCAAGTGTCGCCGCCG

CTTCCACAGGGCTCTGGCTGGACGCCGCCGCCGCC

GCTGCCACCGCCTCTGATCCAAGCCACCTCCCGCC

AGGTGAGCCCCGAGATCCT

E (SEQ ID NO: 14)
GAGCTTGATCTAGGCAGGGACCACACAGCACTGTC

ACACCTGCCTGCTCTTTAGTAGAGGACTGAAGTGC

GGGGGTGGGGGTACGGGGCCGGAATAGAATGTCTC

TGGGACATCTTGGCAAACAGCAGCCGGAAGCAAAG

GGGCAGCTGTGCAAACGGCTCAGGCAGGTGATGGA

TGGCAGGGTAGGAAGGGGGAGGTCCAGAGGTCTGG

ATGGAGGCTTC

Full Calcitonin Promoter Tested (SEQ ID NO: 15)
GGGTGTCGTGCTAAGAAATTTCGACGCTTCTGGGG

ACTGAGGACAAAGGTGCGGACACGACCCCGGGGTA

CCTGGAGTTCCGTGACTCGCGCCACGGACGGCACA

CCTAGGGGCTAATTTCTGCTCTGCCTCAAAGAACC

TCAAGCTAGAGTCCTTGCCTCCGCCCACAGCCCCG

GGATGCCGCTGCTGCGCTCACCGCACAGGCAGCGC

CCGGACCGGCTGCAGCAGATCGCGCGCTGCGCGTT

CCACCGGGAGATGGTGGAGACGCTGAAAAGCTTCT

TTCTTGCCACTCTGGACGCTGTGGGCGGCAAGCGC

CTTAGTCCCTACCTCTGCTGAGCTGAACGCTCAGG

-continued

```
CACAGTGGAACTGAAACCCGGTTCTGCGGGATGTG

AGAGCTGTTGAGGTCACGCGTAATTGGGTGTGATG

GAGGGCGCCTGTTCGTGATGTGTGCAGGTTTGATG

CAAGCAGGTCATCGTCGTGCGAGTGTGTGGATGCG

ACCGCCCGAGAGACTCGGAGGCAGGCTTGGGACAC

GTTTGAGTGAACACCTCAGGATACTCTTCTGGCCA

GTATCTGTTTTTTAGTGTCTGTGATTCAGAGTGGG

CACATGTTGGGAGACAGTAATGGGTTTGGGTGTGT

GTAAATGAGTGTGACCGGAAGCGAGTGTGAGCTTG

ATCTAGGCAGGGACCACACAGCACTGTCACACCTG

CCTGCTCTTTAGTAGAGGACTGAAGTGCGGGGGTG

GGGGTACGGGGCCGGAATAGAATGTCTCTGGGACA

TCTTGGCAAACAGCAGCCGGAAGCAAAGGGGCAGC

TGTGCAAACGGCTCAGGCAGGTGATGGATGGCAGG

GTAGGAAGGGGGAGGTCCAGAGGTCTGGATGGAGG

CTTCCGCATCTGTACCTTGCAACTCACCCCTCAGG

CCCAGCAGGTCATCGGCCCCCTCCTCACACATGTA

ATGGATCTGAAGAGTACCCCGGGACAGTCCGGGGA

GATGGAGATTCGGAAAGTATCCATGGAGATCTTAC

AGAATCCCCTGTGCGGACCAGGAAACTCTTGTAGA

TCCCTGCCTATCTGAGGCCCAGGCGCTGGGCTGTT

TCTCACAATATTCCTTCAAGATGAGATTGTGGTCC

CCATTTCAAAGATGAGTACACTGAGCCTCTGTGAA

GTTACTTGCCCATGATCACACAACCAGGAATTGGG

CCAACTGTAATTGAACTCCTGTCTAACAAAGTTCT

TGCTCCCAGCTCCGTCTCTTGTTTCCCACGAGCCC

TGGCCCTCTGTGGGTAATACCAGCTACTGGAGTCA

GATTTCTTGGGCCCAGAACCCACCCTTAGGGGCAT

TAACCTTTAAAATCTCACTTGGGCAGGGGTCTGGG

ATCAGAGTTGGAAGAGTCCCTACAATCCTGGACCC

TTTCCGCCAAATCGTGAAACCAGGGGTGGAGTGGG

GCGAGGGTTCAAAACCAGGCCGGACTGAGAGGTGA

AATTCACCATGACGTCAAACTGCCCTCAAATTCCC

GCTCACTTTAAGGGCGTTACTTGTTGGTGCCCCCA

CCATCCCCCACCATTTCCATCAATGACCTCAATGC

AAATACAAGTGGGACGGTCCTGCTGGATCCTCCAG

GTTCTGGAAGCATGAGGGTGACGCAACCCAGGGGC

AAAGGACCCCTCCGCCCATTGGTTGCTGTGCACTG

GCGGAACTTTCCCGACCCACAGCGGCGGGAATAAG

AGCAGTCGCTGGCGCTGGGAGGCATCAGAGACACT
```

-continued

```
GCCCAGCCCAAGTGTCGCCGCCGCTTCCACAGGGC

TCTGGCTGGACGCCGCCGCCGCCGCTGCCACCGCC

TCTGATCCAAGCCACCTCCCGCCAGGTGAGCCCCG

AGATCCTG
```

Figure 2A:
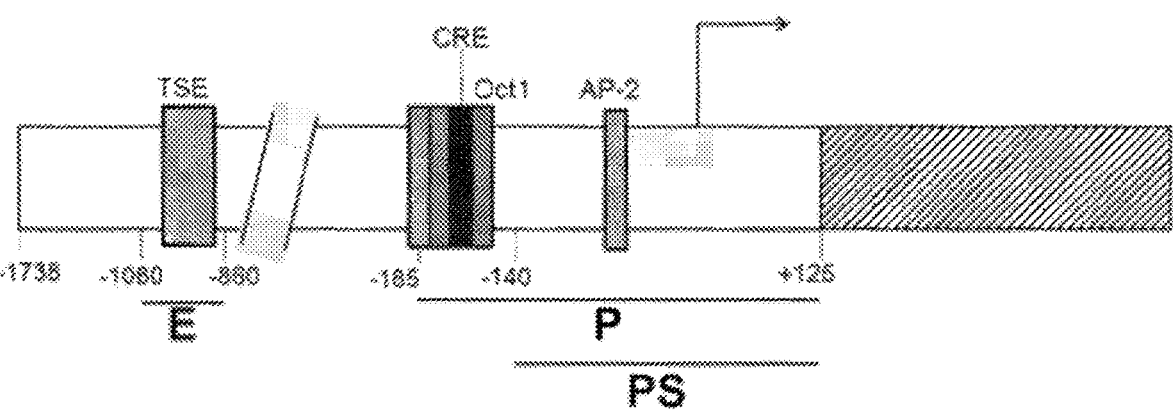
FIGS. 2A, 2B, and 2C are a diagram and two graphs that show characterization of the calcitonin promoter and enhancer regions in MTC and non-MTC cell lines.
Figure 2B:
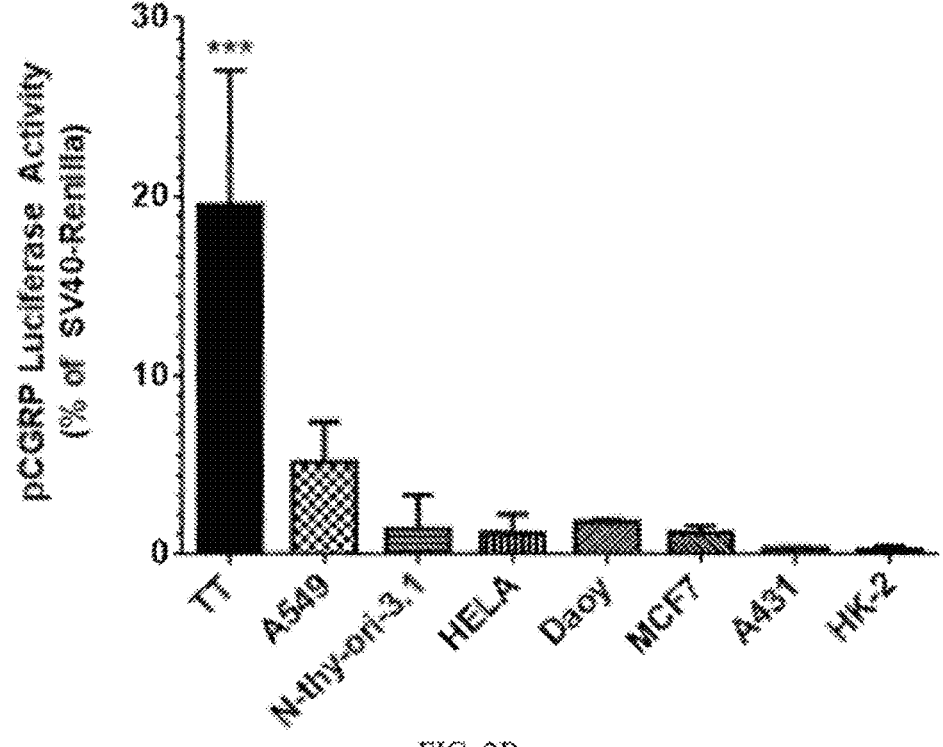
Figure 2C:
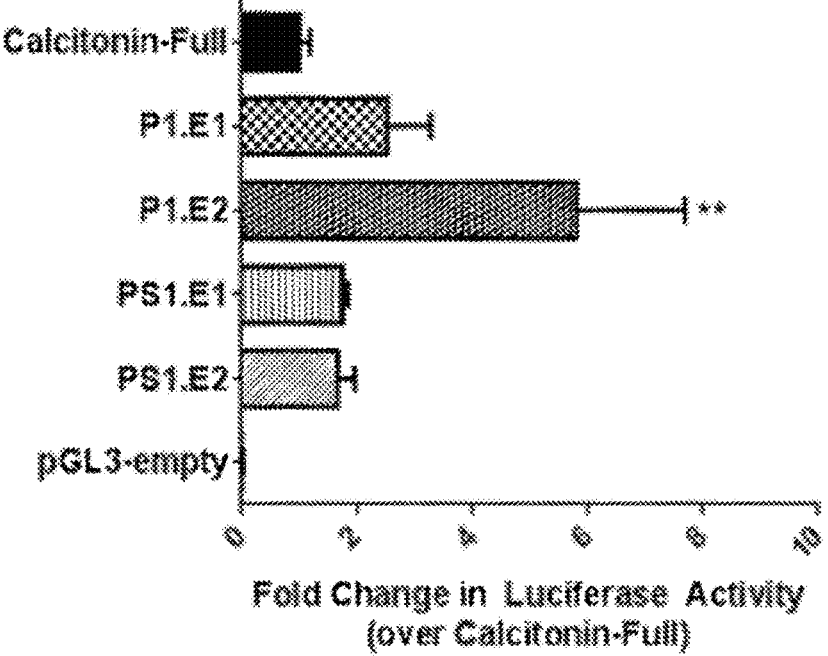
Figure 3A:
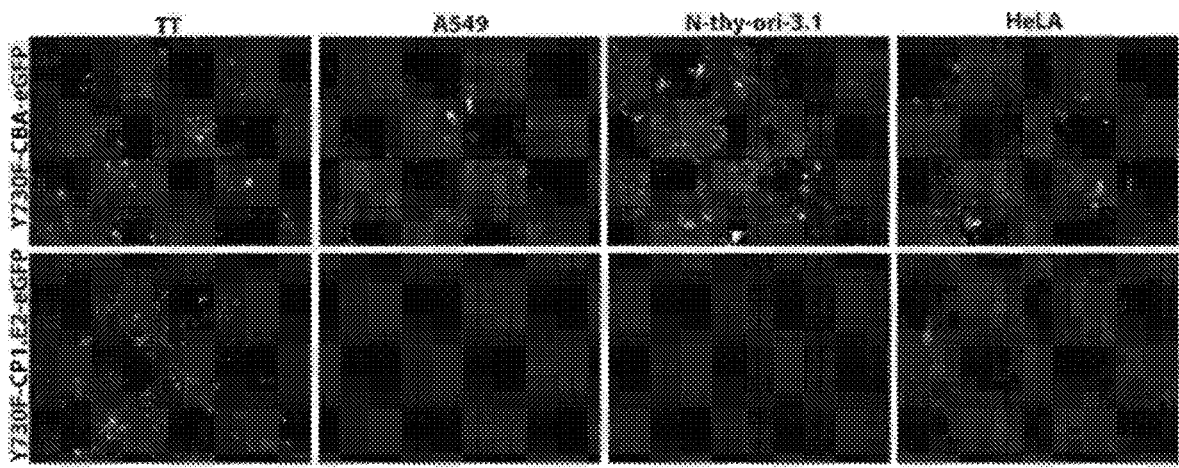
FIGS. 3A, 3B, 3C and 3D are a series of photographs and graphs showing flow cytometry analysis of dsAAV2-Y730E-CBA or -Calcitonin P1.E2 transduced cells.

FIG. 2A depicts the calcitonin promoter regions based on previously published sequence analysis, with relevant transcription factor binding sites and regions highlighted (22). A previous report demonstrated that truncated versions of the calcitonin core promoter combined with tissue-specific enhancer (TSE) regions could increase expression in C cells (23). To confirm specificity of the calcitonin promoter for C cells, the promoter region 1.7 kb upstream of the transcriptional start site was cloned into a luciferase expression vector and tested in TT cells compared to non-C cell-derived cells. As shown in FIG. 2B, luciferase expression from the full calcitonin promoter was significantly higher in TT cells compared to cells derived from the lung, thyroid epithelial, cervix, brain, breast, skin, and kidney. Values are shown as a percentage of the calcitonin promoter divided by co-transfected SV40-*Renilla*. Changes in expression levels were evaluated in TT cells transfected with a luciferase expression vector containing either the full length calcitonin promoter, the proximal promoter with a single or duplicate enhancer region (P1.E1 and P1.E2), or a truncated proximal promoter region lacking the CRE/Oct1 binding sites and single or duplicate enhancer regions (PS1.E1 or PS1.E2). The proximal promoter region (P) containing duplicate enhancer sequences (P1.E2) increased luciferase expression approximately 5-fold in TT cells compared to the full calcitonin promoter region (FIG. 2C). This promoter construct with duplicate enhancer regions provides significantly improved expression in MTC-derived cells. The P1.E2 calcitonin promoter (CP1.E2) was then packaged into a dsAAV2-Y730F mutant vector expressing eGFP. TT cells, as well as A549, Nthy-ori 3-1, and HeLa cells, were evaluated by flow cytometry for specific transduction from the dsAAV2-Y730E-CP1.E2-eGFP vector. Visualization of eGFP expression from this vector is shown compared to a dsAAV2-Y730E-CBA-eGFP positive control (FIG. 3A). Quantification of flow cytometry results are shown in FIG. 3B.

Approximately 10% of TT cells were eGFP positive when transduced with either vector, with no significant difference seen between promoters. While the number of TT cells transduced is relatively low, the expression level of eGFP in positive cells was similar when expressed from either the CBA or CP1.E2 promoters and was of a similar intensity to eGFP expression from the CBA promoter visualized in other cell lines (FIG. 3A).

Figure 3B:
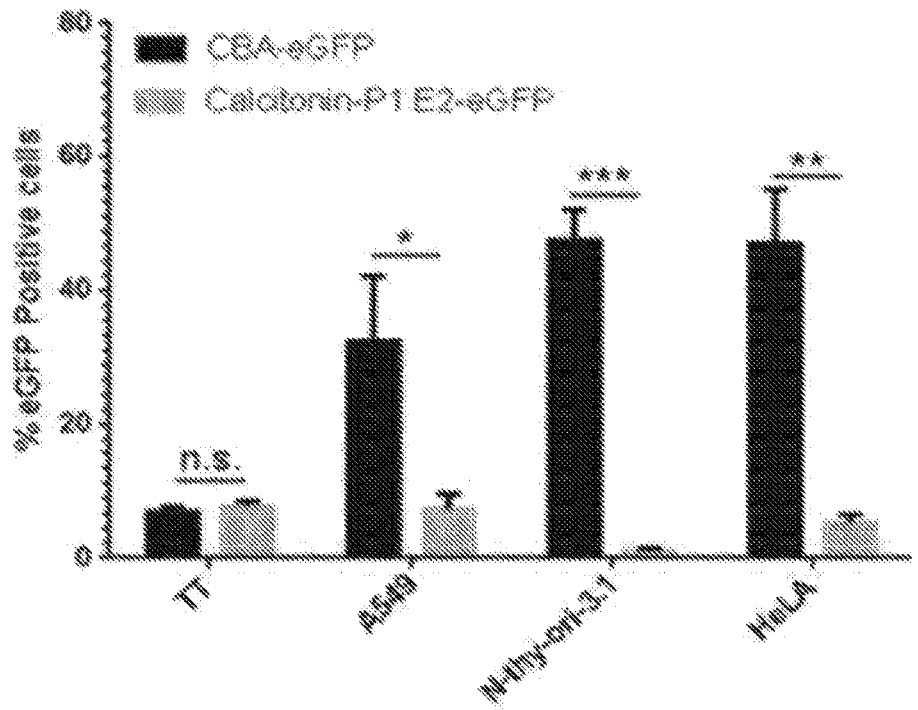
Figure 3C:
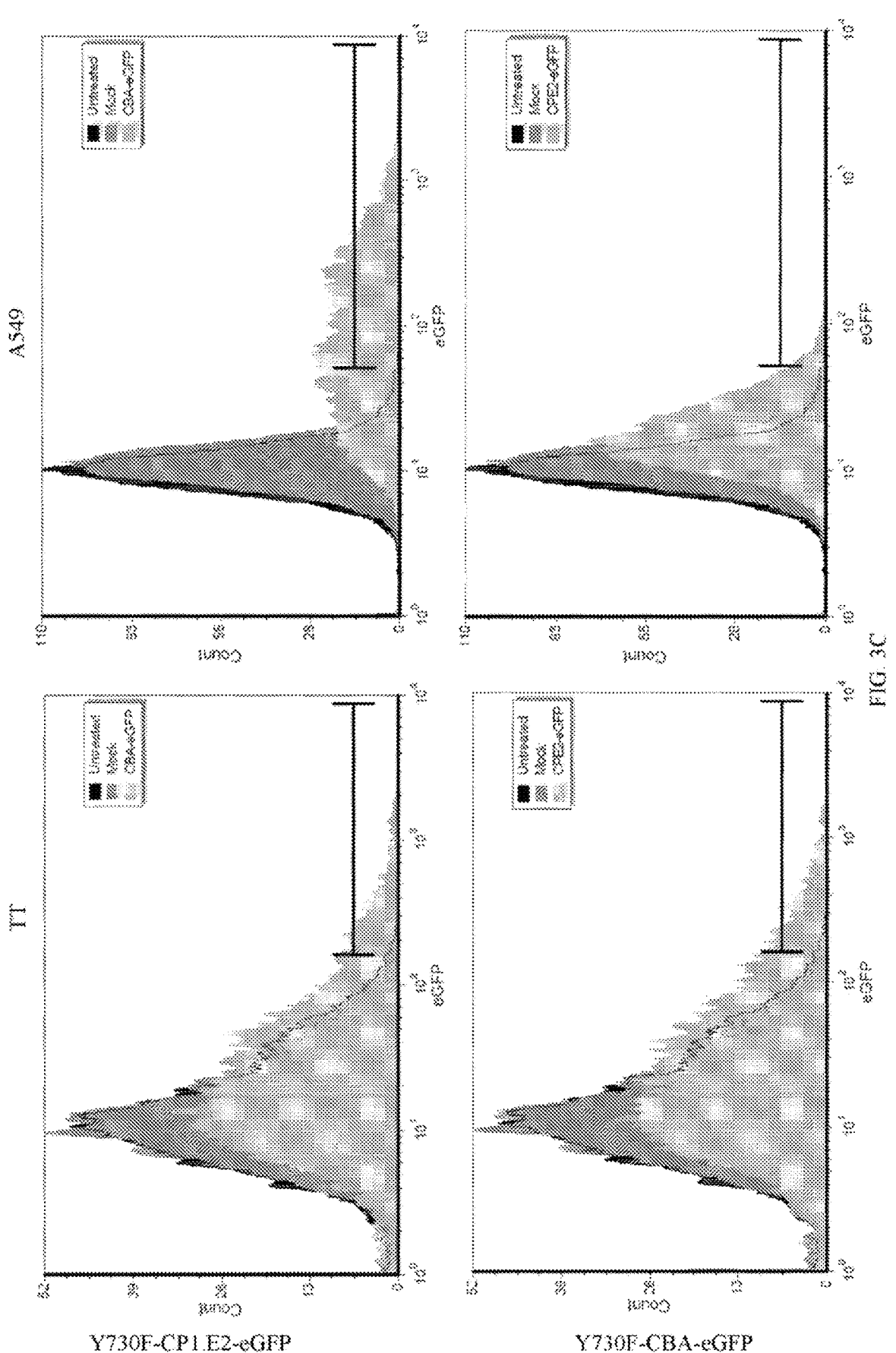
Figure 3D:
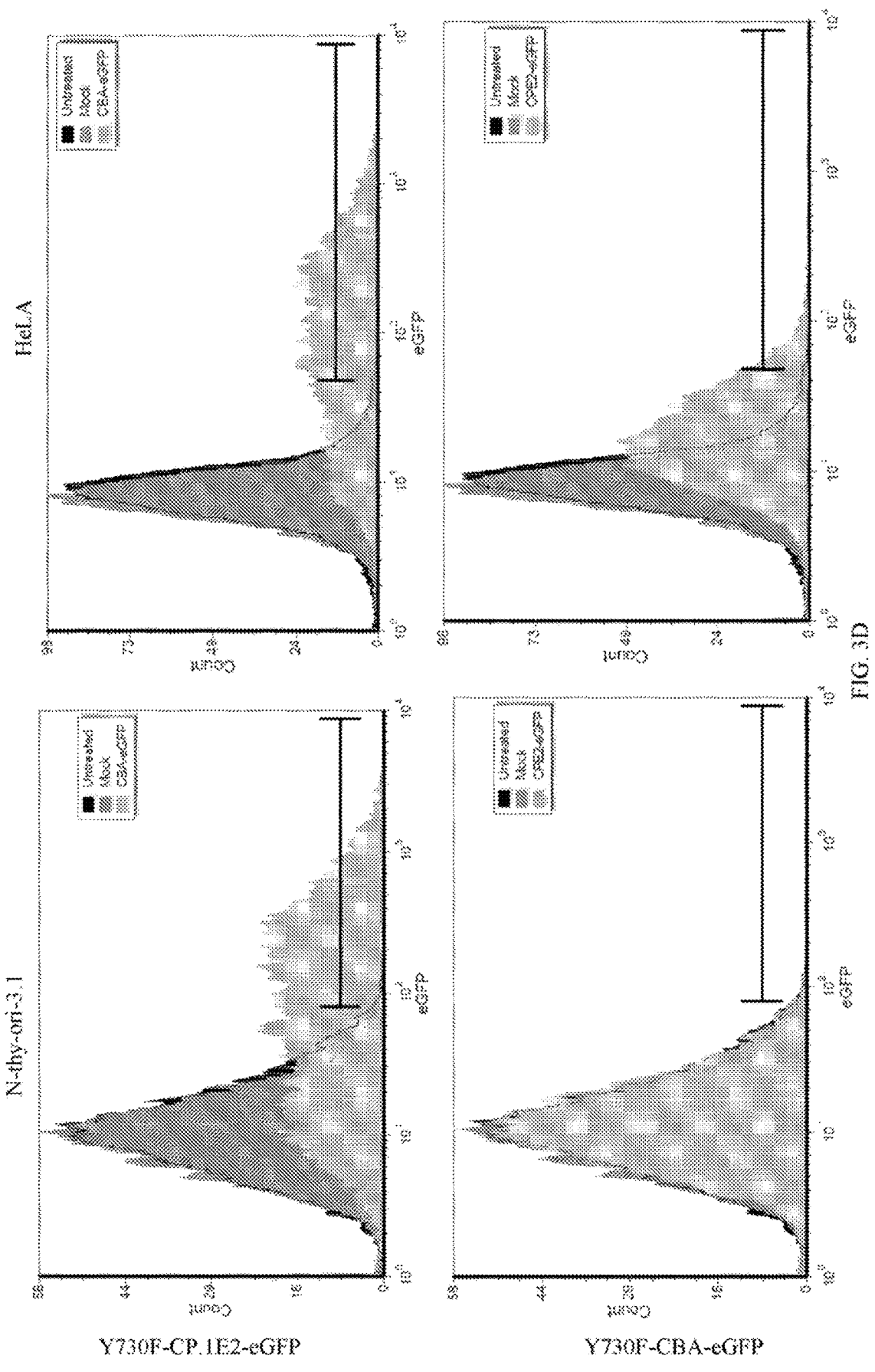

In the three other non-C cell lines examined, there was a significant decrease in eGFP positive cells when transduced with the CP1.E2 vector compared to the CBA control (FIG. 3B). Whereas flow cytometry detected eGFP positive cells in the A549 and HeLa cell lines, expression levels were low and hardly visible by fluorescence microscopy. Representative histograms for each cell line and vector are shown in FIGS. 3C-3D. FIG. 5 provides further data showing infection efficiencies (as a relative change in GFP expression compared to wild-type rAAV2) of rAAV2(Y730F), rAAV2 (S662V), rAAV2(T491V), rAAV2(S662V+T491V), rAAV2 (Y444F+Y500F+Y730F) (M3), and rAAV2(M3+T491V).

These data demonstrate that rAAV2 mutant capsids combined with a modified calcitonin promoter can achieve expression levels similar to the control CBA promoter but also with specificity for MTC-derived cells.

Expression and Localization of Mutant rAAV2 Expressing eGFP In Vivo

To determine whether the capsid-mutated rAAV2 vector containing a modified calcitonin promoter was expressed in vivo, TT cells were used to generate mice containing human MTC tumor xenografts. Tumors of 9-10 mm in diameter (approximately 6-8 weeks post-TT cell inoculation) were injected with $2 \times 10^{10}$ vgs of dsAAV2-Y730E-CBA-eGFP or dsAAV2-Y730E-CP1.E2 or an equal volume of PBS. Two days following vector injection, tumors were resected and evaluated.

Staining of the tumor tissue by H&E demonstrated analogous histological features to MTC with notable vascularization and strong staining for calcitonin (FIGS. 4A and 4B). When evaluated for eGFP expression, positive staining was observed in both dsAAV2-Y730E-CBA and -CP1.E2 injected tumors. Positively stained cells with the strongest expression were observed near the injection site, with sporadic staining of positive cells throughout the tumor section equivalent to approximately 10-15% of MTC cells. FIG. 4C shows a representative image of positive eGFP IHC staining in a dsAAV-Y730E-CP1.E2-eGFP injected tumor, with lack of staining observed in the IgG control (FIG. 4D). All mock-injected tumors were negative for eGFP staining. This observation demonstrates that capsid-mutated rAAV containing a modified calcitonin promoter was capable of expressing in TT cells both in vitro and in vivo.

In some aspects, the results reported here reveal a novel rAAV vector that transduces MTC both in vitro and in vivo. The use of capsid mutant rAAV2 vectors increased transduction in the MTC cell line TT. Development of a shortened, modified calcitonin promoter further increased transgene expression and conferred specificity for MTC cells. These vectors were then shown to transduce MTC cells in a tumor xenograft model. This is believed to be the first demonstration of a rAAV vector transduction of MTC in vivo. Expression of the rAAV in vivo demonstrates this vector could be further optimized for the delivery of therapeutic genes to tumor tissues.

Approximately 10-15% of TT cells were transduced in vitro and in vivo by the vectors tested here. A previous report examining rAAV transduction in TT cells in vitro reported 40% efficiency, but this was performed with an adenovirus co-infection (11). Although the transduction efficiency is lower for the rAAV vectors reported here, transgene expression with rAAV alone is more pertinent and safer for clinical application. Furthermore, previous work has demonstrated that the parent cell line TT contains multiple cell types and expresses proteins at varied levels, including differences in calcitonin expression (24). Additional studies examining the single cell types within the cell line TT may improve the targeting and transduction, and ultimately treatment, of MTC with rAAV.

The use of the truncated calcitonin promoter containing repeated enhancer elements gives improved, specific expression in MTC cells in vitro. The small size of approximately 800 base pairs of this modified calcitonin promoter compared to the 1.7 kb full calcitonin upstream region allows for the capability of packaging larger therapeutic genes in a double-stranded vector. Furthermore, the use of repeated enhancer elements increased expression from transgenes packaged with this promoter as shown in FIG. 1C. This modified promoter could be utilized to strongly express a wide range of transgenes specifically in MTC cells. Multiple methods have been proposed for gene therapy approaches for treatment of thyroid carcinomas including targeting of specific pathways, reintroduction of the sodium iodine symporter, immune modulation, and gene-directed enzyme/prodrug therapy (GDEPT; 8). As the RET gene is commonly mutated in both hereditary and sporadic MTC, drug treatment inhibiting the RET pathway has been used (25-27). Improved, specific methods of inhibiting RET could be delivered using rAAV vectors but would require a high percentages of cells being transduced. Many GDEPT methods not only induce cell death in targeted cells, but result in bystander killing of surrounding cells due to the release of toxic metabolites (28). While the rAAV vector reported here specifically targets MTC cells, only approximately 10% of cells showed transgene expression. A GDEPT method may be beneficial in targeting tumors using rAAV without 100% transduction efficiency being necessary for tumor cytotoxicity.

In some aspects, this study reports use of a rAAV vector for in vivo expression in MTC. Accordingly, in some embodiments, rAAV vectors described herein allow for improved targeting and expression in primary and metastatic MTC tumors, the latter particularly important for developing novel cures for MTC (29). Reliable and specific expression can be achieved in MTC cells due to the use of the modified calcitonin reporter employed here.

REFERENCES

1. Gimm O 2001 Thyroid Cancer. Cancer Letters 163(2): 143-156.
2. Schlumberger M J 1998 Papillary and follicular thyroid carcinoma. NEJM 338(5): 297-306.
3. Carling T, Udelsman R 2014 Thyroid Cancer. Annu Rev Med 65: 125-137.
4. Roy M, Chen H, Sippel R S 2013 Current Understanding and Management of Medullary Thyroid Cancer. Oncologist 18(10): 1093-1100.
5. Gharib H, McConahey W M, Tiegs R D, Bergstralh E J, Goellner J R, Grant C S, van Heerden J A, Sizemore G W, Hay I D 1992 Medullary thyroid carcinoma: clinicopathologic features and long-term follow-up of 65 patients treated during 1946 through 1970. Mayo Clin Proc 67(10): 934-40.
6. Pazaitou-Panayiotou K, Chrisoulidou A, Mandanas S, Tziomalos K, Doumala E, Patakiouta F 2014 Predictive factors that influence the course of medullary thyroid carcinoma. Int J Clin Oncol 19(3): 445-51.
7. Massicotte M H, Brassard M, Claude-Desroches M, Borget I, Bonichon F, Giraudet A L, Do Cao C, Chougnet C N, Leboulleux S, Baudin E, Schlumberger M, de la Fouchardière C 2014 Tyrosine kinase inhibitor treatments in patients with metastatic thyroid carcinomas: a retrospective study of the TUTHYREF network. Eur J Endocrinol 170(4): 575-82.
8. Spitzweg C, Morris J C 2004 Gene therapy for thyroid cancer: current status and future prospects. Thyroid 14(6): 424-34.
9. Li C, Bowles D E, van Dyke T, Samulski R J 2005 Adeno-associated virus vectors: potential applications for cancer gene therapy. Cancer Gene Ther 12(12): 913-25.
10. Luo J, Luo Y, Sun J, Zhou Y, Zhang Y, Yang X 2015 Adeno-associated virus-mediated cancer gene therapy: Current status. Cancer Lett January 356(2PB):347-356 Epub ahead of print
11. Jiang S, Altmann A, Grimm D, Kleinschmidt J A, Schilling T, Germann C, Haberkorn U 2001 Tissue-specific gene expression in medullary thyroid carcinoma cells employing calcitonin regulatory elements and AAV vectors. Cancer Gene Ther 8(7): 469-72.

12. Wu Z, Asokan A, Samulski R J 2006 Adeno-associated virus serotypes: vector toolkits for human gene therapy. Mol Ther 14(3): 316-327.

13. Rabinowitz J E, Rolling F, Li C, Conrath H, Xiao W, Xiao X, Samulski R J 2002 Cross-packaging of a single adeno-associated virus (AAV) type 2 vector genome into multiple AAV serotypes enables transduction with broad specificity. J Virol 76(2): 791-801.

14. Gray S J, Foti S B, Schwartz J W, Bachaboina L, Taylor-Blake B, Coleman J, Ehlers M D, Zylka M J, McCown T J, Samulski R J 2011 Optimizing promoters for recombinant adeno-associated virus-mediated gene expression in the peripheral and central nervous system using self-complementary vectors. Hum Gene Ther 22(9): 1143-53.

15. Orlandi F, Caraci P, Mussa A, Saggiorato E, Pancani G, Angeli A 2001 Treatment of medullary thyroid carcinoma: an update. Endocr Relat Cancer 8:135-147

16. Carruthers K H, Metzger G, During M J, Muravlev A, Wang C, Kocak E 2014 Gene-directed enzyme prodrug therapy for localized chemotherapeutics in allograft and xenograft tumor models. Cancer Gene Ther 21(10): 434-40.

17. Zhong L, Zhao W, Wu J, Maina N, Han Z, Srivastava A 2006 Adeno-associated virus-mediated gene transfer in hematopoietic stem/progenitor cells as a therapeutic tool. Curr Gene Ther 6(6): 683-98.

18. Wang F, Cui X, Wang M, Xiao W, Xu R 2013 A reliable and feasible qPCR strategy for titrating AAV vectors. Med Sci Monit Basic Res 19: 187-93.

19. Adamson L A, Fowler L J, Ewald A S, Clare-Salzler M J, Hobbs J A 2013 Infection and persistence of erythrovirus B19 in benign and cancerous thyroid tissues. J Med Virol 86(9): 1614-20.

20. Adamson-Small L A, Fowler L J, Hobbs J A 2014 Parvovirus B19 Persistence in Abnormal Thyroid Tissue of a Mature Cystic Ovarian Teratoma: A Case Report. Endocr Pathol 25(3): 339-43.

21. Aslanidi G V, Rivers A E, Ortiz L, Song L, Ling C, Govindasamy L, Van Vliet K, Tan M, Agbandje-McKenna M, Srivastava A 2013 Optimization of the Capsid of Recombinant Adeno-Associated Virus 2 (AAV2) Vectors: The Final Threshold? PLoS ONE 8(3): e59142.

22. Monla Y T, Peleg S, Gagel R F, Monia Y T 1995 Cell type-specific regulation of transcription by cyclic adenosine 3,'5'-monophosphate-responsive elements within the calcitonin promoter. Mol Endocrinol 9(7): 784-793.

23. Messina M, Yu D M, Learoyd D L, Both G W, Molloy P L, Robinson B G 2000 High level, tissue-specific expression of a modified calcitonin/calcitonin gene-related peptide promoter in a human medullary thyroid carcinoma cell line. Mol Cell Endocrinol 164(1-2): 219-24.

24. Berger C L, de Bustros A, Roos B A, Leong S S, Mendelsohn G, Gesell M S, Baylin S B 1984 Human medullary thyroid carcinoma in culture provides a model relating growth dynamics, endocrine cell differentiation, and tumor progression. J Clin Endocrinol Metab 59(2): 338-43.

25. Grabowski P, Briest F, Baum R P, Zaknun J J, Kulkarni H R, Zeitz M Horsch D 2012 Vandetanib therapy in medullary thyroid cancer. Drugs Today (Barc) 48(11): 723-33.

26. Elisei R, Cosci B, Romei C, Bottici V, Renzini G, Molinaro E, Agate L, Vivaldi A, Faviana P, Basolo F, Miccoli P, Berti P, Pacini F, Pinchera A 2008 Prognostic significance of somatic RET oncogene mutations in sporadic medullary thyroid cancer: a 10-year follow-up study. J Clin Endocrinol Metab 93(3): 682-7.

27. Plaza-Menacho I, Mologni L, McDonald N Q 2014 Mechanisms of RET signaling in cancer: current and future implications for targeted therapy. Cell Signal 26(8): 1743-52.

28. Dachs G U, Hunt M A, Syddall S, Singleton D C, Patterson A V 2009 Bystander or no bystander for gene directed enzyme prodrug therapy. Molecules 14(11): 4517-45.

29. Messina M, Robinson B G 2007 Technology insight: gene therapy and its potential role in the treatment of medullary thyroid carcinoma. Nat Clin Pract Endocrinol Metab 3(3): 290-301.

30. Frendo J L, Delage-Mourroux R, Cohen R, Pichaud F, Pidoux E, Guliana J M, Jullienne A 1998 Calcitonin receptor mRNA is expressed in human medullary thyroid carcinoma. Thyroid 8(2): 141-7.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

What is claimed is:

1. A method of delivering a nucleic acid to a medullary thyroid carcinoma cell, the method comprising:

administering to a medullary thyroid carcinoma cell a rAAV2 particle comprising:

(a) a modified capsid protein comprising a non-native amino acid substitution at a position that corresponds to a surface-exposed amino acid in a wild-type AAV2 capsid protein; and (b) a nucleic acid comprising an expression construct containing a promoter operably linked to a coding sequence of a gene of interest, wherein the promoter is a truncated calcitonin promoter consisting of the nucleic acid sequence of SEQ ID NO: 1.

2. The method of claim 1, wherein the non-native amino acid substitution is selected from:

(a) a non-tyrosine amino acid at Y730, (b) a non-serine amino acid at S662, (c) a non-threonine amino acid at T491, (d) a non-serine amino acid at S662 and a non-threonine amino acid at T491, (e) a non-tyrosine amino acid at Y444, a non-tyrosine amino acid at Y500, and a non-tyrosine amino acid at Y730, or (f) a non-tyrosine amino acid at Y444, a non-tyrosine amino acid at Y500, a non-tyrosine amino acid at Y730 and a non-threonine amino acid at T491;

wherein each substitution is relative to the wild-type AAV2 sequence given as SEQ ID NO: 2.

3. The method of claim 2, wherein the non-native amino acid substitution is selected from:

(a) Y730F, (b) S662V, (c) T491V, (d) S662V and T491V, (e) Y444F, Y500F, and Y730F, or (f) Y444F, Y500F, Y730F and T491V.

4. The method of claim 3, wherein the non-native amino acid substitution is selected from (a) Y730F or (e) Y444F, Y500F, and Y730F.

5. The method of claim 1, wherein the gene of interest is CYP2B6.

6. The method of claim 1, wherein the expression construct further comprises a tissue-specific enhancer region of the calcitonin gene having the sequence of nucleotides 980 to 1200 of SEQ ID NO: 3, and wherein the enhancer region is positioned 5' of the truncated calcitonin promoter.

7. The method of claim 1, wherein the expression construct is flanked on each side by an AAV2 inverted terminal repeat sequence (ITR).

8. The method of claim 1, wherein the medullary thyroid carcinoma cell is in a human subject.

9. The method of claim 8, wherein the human subject has metastatic medullary thyroid carcinoma.

10. A method of treating medullary thyroid carcinoma in a subject comprising administering to the subject:

(i) an rAAV2 particle comprising (a) a modified capsid protein comprising a non-native amino acid substitution at a position that corresponds to a surface-exposed amino acid in a wild-type AAV2 capsid protein, and (b) a nucleic acid comprising an expression construct containing a promoter operably linked to a coding sequence of a gene of interest, wherein the gene of interest is CYP2B6 wherein the promoter is a truncated calcitonin promoter consisting of the nucleic acid sequence of SEQ ID NO: 1; and (ii) cyclophosphamide.

* * * * *